(12) United States Patent
Vandine et al.

(10) Patent No.: US 8,789,529 B2
(45) Date of Patent: Jul. 29, 2014

(54) METHOD FOR VENTILATION

(75) Inventors: Joseph D. Vandine, Manteca, CA (US); David Hyde, Oceanside, CA (US); Warren G. Sanborn, Escondido, CA (US)

(73) Assignee: Covidien LP, Mansfield, MA (US)

( * ) Notice: Subject to any disclaimer, the term of this patent is extended or adjusted under 35 U.S.C. 154(b) by 501 days.

(21) Appl. No.: 12/844,967

(22) Filed: Jul. 28, 2010

(65) Prior Publication Data

US 2011/0041850 A1 Feb. 24, 2011

Related U.S. Application Data

(60) Provisional application No. 61/235,588, filed on Aug. 20, 2009.

(51) Int. Cl.
*A61M 16/00* (2006.01)
*F16K 31/02* (2006.01)
*A61B 7/00* (2006.01)

(52) U.S. Cl.
USPC .................................................. 128/204.23

(58) Field of Classification Search
USPC ............ 128/204.23, 204.18, 204.21, 204.26, 128/204.22; 600/529, 532, 533, 538
See application file for complete search history.

(56) References Cited

U.S. PATENT DOCUMENTS

| | | | |
|---|---|---|---|
| 3,805,780 A | 4/1974 | Cramer et al. | |
| 3,941,124 A | 3/1976 | Rodewald et al. | |
| 4,056,098 A | 11/1977 | Michel et al. | |
| 4,305,388 A | 12/1981 | Brisson | |
| 4,340,044 A | 7/1982 | Levy et al. | |
| 4,752,089 A | 6/1988 | Carter | |
| 4,921,642 A | 5/1990 | LaTorraca | |
| 4,939,647 A | 7/1990 | Clough et al. | |
| 4,954,799 A | 9/1990 | Kumar | |
| 4,971,052 A | 11/1990 | Edwards | |
| 4,986,268 A | 1/1991 | Tehrani | |
| 5,057,822 A | 10/1991 | Hoffman | |
| 5,072,737 A | 12/1991 | Goulding | |
| 5,094,235 A | 3/1992 | Westenskow et al. | |
| 5,150,291 A | 9/1992 | Cummings et al. | |

(Continued)

FOREIGN PATENT DOCUMENTS

| | | |
|---|---|---|
| WO | WO2004000114 | 12/2003 |
| WO | WO2007085110 | 8/2007 |
| WO | WO2007145948 | 12/2007 |

OTHER PUBLICATIONS

Medicina Intensiva 33.6 (Aug. 2009-Sep. 2009): 269-275.*

(Continued)

*Primary Examiner* — Kristen Matter
*Assistant Examiner* — Mark Wardas

(57) ABSTRACT

The disclosure describes a method for automatically initiating ventilation, controlling ventilation, transitioning a ventilator to subject controlled ventilation, and weaning a subject from ventilation. The disclosure describes that the method for automatically initiating ventilation includes inputting a physical characteristic of the subject into a ventilator. The physical characteristic may be ideal body weight, height, or age. Based on the inputted physical characteristic, one or more ventilation parameters are calculated. The disclosure describes initiating ventilation based on the calculated parameters. During ventilation at least one physiological parameter of the subject is monitored. At least one ventilation parameter may be adjusted based on the monitoring of the physiological parameters and the inputted physical characteristic.

8 Claims, 14 Drawing Sheets

(56) References Cited

U.S. PATENT DOCUMENTS

| | | | |
|---|---|---|---|
| 5,161,525 | A | 11/1992 | Kimm et al. |
| 5,237,987 | A | 8/1993 | Anderson et al. |
| 5,271,389 | A | 12/1993 | Isaza et al. |
| 5,279,549 | A | 1/1994 | Ranford |
| 5,299,568 | A | 4/1994 | Forare et al. |
| 5,301,921 | A | 4/1994 | Kumar |
| 5,315,989 | A | 5/1994 | Tobia |
| 5,319,540 | A | 6/1994 | Isaza et al. |
| 5,325,861 | A | 7/1994 | Goulding |
| 5,333,606 | A | 8/1994 | Schneider et al. |
| 5,339,807 | A | 8/1994 | Carter |
| 5,343,857 | A | 9/1994 | Schneider et al. |
| 5,351,522 | A | 10/1994 | Lura |
| 5,357,946 | A | 10/1994 | Kee et al. |
| 5,365,922 | A | 11/1994 | Raemer |
| 5,368,019 | A | 11/1994 | LaTorraca |
| 5,383,449 | A | 1/1995 | Forare et al. |
| 5,385,142 | A | 1/1995 | Brady et al. |
| 5,388,575 | A | 2/1995 | Taube |
| 5,390,666 | A | 2/1995 | Kimm et al. |
| 5,398,682 | A | 3/1995 | Lynn |
| 5,401,135 | A | 3/1995 | Stoen et al. |
| 5,402,796 | A | 4/1995 | Packer et al. |
| 5,407,174 | A | 4/1995 | Kumar |
| 5,413,110 | A | 5/1995 | Cummings et al. |
| 5,429,123 | A | 7/1995 | Shaffer et al. |
| 5,438,980 | A | 8/1995 | Phillips |
| 5,443,075 | A | 8/1995 | Holscher |
| 5,503,147 | A | 4/1996 | Bertheau |
| 5,513,631 | A | 5/1996 | McWilliams |
| 5,517,983 | A | 5/1996 | Deighan et al. |
| 5,520,071 | A | 5/1996 | Jones |
| 5,524,615 | A | 6/1996 | Power |
| 5,531,221 | A | 7/1996 | Power |
| 5,535,738 | A | 7/1996 | Estes et al. |
| 5,540,220 | A | 7/1996 | Gropper et al. |
| 5,542,415 | A | 8/1996 | Brady |
| 5,544,674 | A | 8/1996 | Kelly |
| 5,549,106 | A | 8/1996 | Gruenke et al. |
| 5,551,419 | A | 9/1996 | Froehlich et al. |
| 5,596,984 | A | 1/1997 | O'Mahoney et al. |
| 5,605,151 | A | 2/1997 | Lynn |
| 5,623,923 | A | 4/1997 | Bertheau et al. |
| 5,630,411 | A | 5/1997 | Holscher |
| 5,632,270 | A | 5/1997 | O'Mahoney et al. |
| 5,645,048 | A | 7/1997 | Brodsky et al. |
| 5,660,171 | A | 8/1997 | Kimm et al. |
| 5,664,560 | A | 9/1997 | Merrick et al. |
| 5,664,562 | A | 9/1997 | Bourdon |
| 5,671,767 | A | 9/1997 | Kelly |
| 5,672,041 | A | 9/1997 | Ringdahl et al. |
| 5,673,689 | A | 10/1997 | Power |
| 5,692,497 | A | 12/1997 | Schnitzer et al. |
| 5,715,812 | A | 2/1998 | Deighan et al. |
| 5,752,509 | A | 5/1998 | Lachmann et al. |
| 5,762,480 | A | 6/1998 | Adahan |
| 5,771,884 | A | 6/1998 | Yarnall et al. |
| 5,791,339 | A | 8/1998 | Winter |
| 5,794,986 | A | 8/1998 | Gansel et al. |
| 5,813,399 | A | 9/1998 | Isaza et al. |
| 5,826,575 | A | 10/1998 | Lall |
| 5,829,441 | A | 11/1998 | Kidd et al. |
| 5,864,938 | A | 2/1999 | Gansel et al. |
| 5,865,168 | A | 2/1999 | Isaza |
| 5,881,717 | A | 3/1999 | Isaza |
| 5,881,723 | A | 3/1999 | Wallace et al. |
| 5,884,623 | A | 3/1999 | Winter |
| 5,891,023 | A | 4/1999 | Lynn |
| 5,909,731 | A | 6/1999 | O'Mahony et al. |
| 5,915,379 | A | 6/1999 | Wallace et al. |
| 5,915,380 | A | 6/1999 | Wallace et al. |
| 5,915,382 | A | 6/1999 | Power |
| 5,918,597 | A | 7/1999 | Jones et al. |
| 5,921,238 | A | 7/1999 | Bourdon |
| 5,934,274 | A | 8/1999 | Merrick et al. |
| 5,937,853 | A * | 8/1999 | Strom ..................... 128/204.23 |
| 6,024,089 | A | 2/2000 | Wallace et al. |
| 6,041,780 | A | 3/2000 | Richard et al. |
| 6,047,860 | A | 4/2000 | Sanders |
| 6,076,523 | A | 6/2000 | Jones et al. |
| 6,116,240 | A | 9/2000 | Merrick et al. |
| 6,116,464 | A | 9/2000 | Sanders |
| 6,123,073 | A | 9/2000 | Schlawin et al. |
| 6,123,074 | A | 9/2000 | Hete et al. |
| 6,135,106 | A | 10/2000 | Dirks et al. |
| 6,142,150 | A | 11/2000 | O'Mahony et al. |
| 6,148,814 | A | 11/2000 | Clemmer et al. |
| 6,158,432 | A | 12/2000 | Biondi et al. |
| 6,161,539 | A | 12/2000 | Winter |
| 6,220,245 | B1 | 4/2001 | Takabayashi et al. |
| 6,223,064 | B1 | 4/2001 | Lynn et al. |
| 6,269,812 | B1 | 8/2001 | Wallace et al. |
| 6,273,444 | B1 | 8/2001 | Power |
| 6,283,119 | B1 | 9/2001 | Bourdon |
| 6,305,373 | B1 | 10/2001 | Wallace et al. |
| 6,321,748 | B1 | 11/2001 | O'Mahoney |
| 6,325,785 | B1 | 12/2001 | Babkes et al. |
| 6,342,039 | B1 | 1/2002 | Lynn et al. |
| 6,357,438 | B1 | 3/2002 | Hansen |
| 6,360,745 | B1 | 3/2002 | Wallace et al. |
| 6,369,838 | B1 | 4/2002 | Wallace et al. |
| 6,371,114 | B1 | 4/2002 | Schmidt et al. |
| 6,390,091 | B1 | 5/2002 | Banner et al. |
| 6,412,483 | B1 | 7/2002 | Jones et al. |
| 6,439,229 | B1 | 8/2002 | Du et al. |
| 6,467,478 | B1 | 10/2002 | Merrick et al. |
| 6,512,938 | B2 | 1/2003 | Claure et al. |
| 6,532,958 | B1 | 3/2003 | Buan et al. |
| 6,532,959 | B1 | 3/2003 | Berthon-Jones |
| 6,532,960 | B1 | 3/2003 | Yurko |
| 6,536,429 | B1 | 3/2003 | Pavlov et al. |
| 6,543,449 | B1 | 4/2003 | Woodring et al. |
| 6,546,930 | B1 | 4/2003 | Emerson et al. |
| 6,553,991 | B1 | 4/2003 | Isaza |
| 6,557,553 | B1 | 5/2003 | Borrello |
| 6,561,187 | B2 | 5/2003 | Schmidt et al. |
| 6,571,795 | B2 | 6/2003 | Bourdon |
| 6,609,016 | B1 | 8/2003 | Lynn |
| 6,622,726 | B1 | 9/2003 | Du |
| 6,640,806 | B2 | 11/2003 | Yurko |
| 6,644,310 | B1 | 11/2003 | Delache et al. |
| 6,644,312 | B2 | 11/2003 | Berthon-Jones et al. |
| 6,668,824 | B1 | 12/2003 | Isaza et al. |
| 6,671,529 | B2 | 12/2003 | Claure et al. |
| 6,675,801 | B2 | 1/2004 | Wallace et al. |
| 6,688,307 | B2 | 2/2004 | Berthon-Jones |
| 6,718,974 | B1 | 4/2004 | Moberg |
| 6,723,055 | B2 | 4/2004 | Hoffman |
| 6,725,447 | B1 | 4/2004 | Gilman et al. |
| 6,739,337 | B2 | 5/2004 | Isaza |
| 6,748,252 | B2 | 6/2004 | Lynn et al. |
| 6,752,151 | B2 | 6/2004 | Hill |
| 6,758,216 | B1 | 7/2004 | Berthon-Jones et al. |
| 6,760,608 | B2 | 7/2004 | Lynn |
| 6,761,165 | B2 | 7/2004 | Strickland, Jr. |
| 6,761,167 | B1 | 7/2004 | Nadjafizadeh et al. |
| 6,761,168 | B1 | 7/2004 | Nadjafizadeh et al. |
| 6,796,305 | B1 | 9/2004 | Banner et al. |
| 6,814,074 | B1 | 11/2004 | Nadjafizadeh et al. |
| 6,820,618 | B2 | 11/2004 | Banner et al. |
| 6,837,242 | B2 | 1/2005 | Younes |
| 6,866,040 | B1 | 3/2005 | Bourdon |
| 6,868,346 | B2 | 3/2005 | Larson et al. |
| 6,960,854 | B2 | 11/2005 | Nadjafizadeh et al. |
| 7,008,380 | B1 | 3/2006 | Rees et al. |
| 7,036,504 | B2 | 5/2006 | Wallace et al. |
| 7,066,173 | B2 | 6/2006 | Banner et al. |
| 7,077,131 | B2 | 7/2006 | Hansen |
| 7,081,095 | B2 | 7/2006 | Lynn et al. |
| RE39,225 | E | 8/2006 | Isaza et al. |
| 7,089,936 | B2 | 8/2006 | Madaus et al. |
| 7,089,937 | B2 | 8/2006 | Berthon-Jones et al. |
| 7,092,757 | B2 | 8/2006 | Larson et al. |
| 7,100,609 | B2 | 9/2006 | Berthon-Jones et al. |

(56) References Cited

U.S. PATENT DOCUMENTS

| | | | |
|---|---|---|---|
| 7,117,438 B2 | 10/2006 | Wallace et al. | |
| 7,152,598 B2 | 12/2006 | Morris et al. | |
| 7,210,478 B2 | 5/2007 | Banner et al. | |
| 7,229,430 B2 | 6/2007 | Hickle et al. | |
| 7,267,122 B2 | 9/2007 | Hill | |
| 7,270,126 B2 | 9/2007 | Wallace et al. | |
| 7,275,540 B2 | 10/2007 | Bolam et al. | |
| 7,296,573 B2 | 11/2007 | Estes et al. | |
| 7,297,119 B2 | 11/2007 | Westbrook et al. | |
| 7,331,343 B2 | 2/2008 | Schmidt et al. | |
| 7,334,578 B2 * | 2/2008 | Biondi et al. | 128/204.23 |
| 7,353,824 B1 | 4/2008 | Forsyth et al. | |
| 7,369,757 B2 | 5/2008 | Farbarik | |
| 7,370,650 B2 | 5/2008 | Nadjafizadeh et al. | |
| 7,398,115 B2 | 7/2008 | Lynn | |
| 7,406,870 B2 | 8/2008 | Seto | |
| 7,428,902 B2 | 9/2008 | Du et al. | |
| 7,448,381 B2 | 11/2008 | Sasaki et al. | |
| 7,455,583 B2 | 11/2008 | Taya | |
| 7,460,959 B2 | 12/2008 | Jafari | |
| 7,472,702 B2 | 1/2009 | Beck et al. | |
| 7,487,773 B2 | 2/2009 | Li | |
| 7,509,957 B2 | 3/2009 | Duquette et al. | |
| 7,520,279 B2 | 4/2009 | Berthon-Jones | |
| 7,527,054 B2 | 5/2009 | Misholi | |
| 7,654,802 B2 | 2/2010 | Crawford, Jr. et al. | |
| 7,668,579 B2 | 2/2010 | Lynn | |
| 7,694,677 B2 | 4/2010 | Tang | |
| 7,717,113 B2 | 5/2010 | Andrieux | |
| D618,356 S | 6/2010 | Ross | |
| 7,758,503 B2 | 7/2010 | Lynn et al. | |
| 7,784,461 B2 | 8/2010 | Figueiredo et al. | |
| 7,802,571 B2 | 9/2010 | Tehrani | |
| 7,823,588 B2 | 11/2010 | Hansen | |
| 7,855,716 B2 | 12/2010 | McCreary et al. | |
| D632,796 S | 2/2011 | Ross et al. | |
| D632,797 S | 2/2011 | Ross et al. | |
| 7,891,354 B2 | 2/2011 | Farbarik | |
| 7,893,560 B2 | 2/2011 | Carter | |
| D638,852 S | 5/2011 | Skidmore et al. | |
| 7,984,714 B2 | 7/2011 | Hausmann et al. | |
| D643,535 S | 8/2011 | Ross et al. | |
| 7,992,557 B2 | 8/2011 | Nadjafizadeh et al. | |
| 8,001,967 B2 | 8/2011 | Wallace et al. | |
| D645,158 S | 9/2011 | Sanchez et al. | |
| 8,021,310 B2 | 9/2011 | Sanborn et al. | |
| D649,157 S | 11/2011 | Skidmore et al. | |
| D653,749 S | 2/2012 | Winter et al. | |
| 8,113,062 B2 | 2/2012 | Graboi et al. | |
| D655,405 S | 3/2012 | Winter et al. | |
| D655,809 S | 3/2012 | Winter et al. | |
| 8,181,648 B2 | 5/2012 | Perine et al. | |
| 8,210,173 B2 | 7/2012 | Vandine | |
| 8,210,174 B2 | 7/2012 | Farbarik | |
| 8,240,684 B2 | 8/2012 | Ross et al. | |
| 8,267,085 B2 | 9/2012 | Jafari et al. | |
| 8,272,379 B2 | 9/2012 | Jafari et al. | |
| 8,272,380 B2 | 9/2012 | Jafari et al. | |
| 8,302,600 B2 | 11/2012 | Andrieux et al. | |
| 8,302,602 B2 | 11/2012 | Andrieux et al. | |
| 2002/0185126 A1 | 12/2002 | Krebs | |
| 2005/0039748 A1 | 2/2005 | Andrieux | |
| 2005/0139212 A1 | 6/2005 | Bourdon | |
| 2005/0172965 A1 | 8/2005 | Thulin | |
| 2006/0112959 A1 | 6/2006 | Mechlenburg et al. | |
| 2006/0155206 A1 | 7/2006 | Lynn | |
| 2006/0155207 A1 | 7/2006 | Lynn et al. | |
| 2006/0161071 A1 | 7/2006 | Lynn et al. | |
| 2006/0189880 A1 | 8/2006 | Lynn et al. | |
| 2006/0195041 A1 | 8/2006 | Lynn et al. | |
| 2006/0235324 A1 | 10/2006 | Lynn | |
| 2006/0241708 A1 | 10/2006 | Boute | |
| 2006/0264762 A1 | 11/2006 | Starr | |
| 2006/0272642 A1 | 12/2006 | Chalvignac | |
| 2007/0000494 A1 | 1/2007 | Banner et al. | |
| 2007/0017515 A1 | 1/2007 | Wallace et al. | |
| 2007/0027375 A1 | 2/2007 | Melker et al. | |
| 2007/0028921 A1 | 2/2007 | Banner et al. | |
| 2007/0044805 A1 | 3/2007 | Wedler et al. | |
| 2007/0072541 A1 | 3/2007 | Daniels, II et al. | |
| 2007/0077200 A1 | 4/2007 | Baker | |
| 2007/0093721 A1 | 4/2007 | Lynn et al. | |
| 2007/0129647 A1 | 6/2007 | Lynn | |
| 2007/0149860 A1 | 6/2007 | Lynn et al. | |
| 2007/0157931 A1 | 7/2007 | Parker et al. | |
| 2007/0163579 A1 | 7/2007 | Li et al. | |
| 2007/0191697 A1 | 8/2007 | Lynn et al. | |
| 2007/0215154 A1 | 9/2007 | Borrello | |
| 2007/0227537 A1 | 10/2007 | Bemister et al. | |
| 2007/0272241 A1 | 11/2007 | Sanborn et al. | |
| 2007/0277823 A1 | 12/2007 | Al-Ali et al. | |
| 2007/0284361 A1 | 12/2007 | Nadjafizadeh et al. | |
| 2008/0000479 A1 | 1/2008 | Elaz et al. | |
| 2008/0053441 A1 | 3/2008 | Gottlib et al. | |
| 2008/0066752 A1 | 3/2008 | Baker et al. | |
| 2008/0066753 A1 | 3/2008 | Martin et al. | |
| 2008/0066754 A1 * | 3/2008 | Faram | 128/204.25 |
| 2008/0072896 A1 | 3/2008 | Setzer et al. | |
| 2008/0072902 A1 | 3/2008 | Setzer et al. | |
| 2008/0078390 A1 | 4/2008 | Milne et al. | |
| 2008/0081974 A1 | 4/2008 | Pav | |
| 2008/0083644 A1 | 4/2008 | Janbakhsh et al. | |
| 2008/0092894 A1 | 4/2008 | Nicolazzi et al. | |
| 2008/0097234 A1 | 4/2008 | Nicolazzi et al. | |
| 2008/0110461 A1 | 5/2008 | Mulqueeny et al. | |
| 2008/0178880 A1 | 7/2008 | Christopher et al. | |
| 2008/0178882 A1 | 7/2008 | Christopher et al. | |
| 2008/0200775 A1 | 8/2008 | Lynn | |
| 2008/0200819 A1 | 8/2008 | Lynn et al. | |
| 2008/0236582 A1 * | 10/2008 | Tehrani | 128/204.22 |
| 2008/0251079 A1 | 10/2008 | Richey | |
| 2008/0314385 A1 | 12/2008 | Brunner et al. | |
| 2009/0165795 A1 | 7/2009 | Nadjafizadeh et al. | |
| 2009/0171176 A1 | 7/2009 | Andersohn | |
| 2009/0171226 A1 | 7/2009 | Campbell et al. | |
| 2009/0205661 A1 | 8/2009 | Stephenson et al. | |
| 2009/0205663 A1 | 8/2009 | Vandine et al. | |
| 2009/0241952 A1 | 10/2009 | Nicolazzi et al. | |
| 2009/0241953 A1 | 10/2009 | Vandine et al. | |
| 2009/0241956 A1 | 10/2009 | Baker, Jr. et al. | |
| 2009/0241957 A1 | 10/2009 | Baker, Jr. | |
| 2009/0241958 A1 | 10/2009 | Baker, Jr. | |
| 2009/0241962 A1 | 10/2009 | Jafari et al. | |
| 2009/0247891 A1 | 10/2009 | Wood | |
| 2009/0301486 A1 | 12/2009 | Masic | |
| 2009/0301487 A1 | 12/2009 | Masic | |
| 2009/0301490 A1 | 12/2009 | Masic | |
| 2009/0301491 A1 | 12/2009 | Masic et al. | |
| 2010/0006098 A1 | 1/2010 | McGinnis et al. | |
| 2010/0011307 A1 | 1/2010 | Desfossez et al. | |
| 2010/0024820 A1 | 2/2010 | Bourdon | |
| 2010/0051026 A1 | 3/2010 | Graboi | |
| 2010/0051029 A1 | 3/2010 | Jafari et al. | |
| 2010/0069761 A1 | 3/2010 | Karst et al. | |
| 2010/0071689 A1 | 3/2010 | Thiessen | |
| 2010/0071692 A1 | 3/2010 | Porges | |
| 2010/0071695 A1 | 3/2010 | Thiessen | |
| 2010/0071696 A1 | 3/2010 | Jafari | |
| 2010/0071697 A1 | 3/2010 | Jafari et al. | |
| 2010/0078017 A1 | 4/2010 | Andrieux et al. | |
| 2010/0078026 A1 | 4/2010 | Andrieux et al. | |
| 2010/0081119 A1 | 4/2010 | Jafari et al. | |
| 2010/0081955 A1 | 4/2010 | Wood, Jr. et al. | |
| 2010/0108064 A1 * | 5/2010 | Blackwell et al. | 128/204.21 |
| 2010/0139660 A1 | 6/2010 | Adahan | |
| 2010/0147303 A1 | 6/2010 | Jafari et al. | |
| 2010/0186742 A1 | 7/2010 | Sherman et al. | |
| 2010/0186744 A1 | 7/2010 | Andrieux | |
| 2010/0218765 A1 | 9/2010 | Jafari et al. | |
| 2010/0218766 A1 * | 9/2010 | Milne | 128/204.23 |
| 2010/0218767 A1 | 9/2010 | Jafari et al. | |
| 2010/0236555 A1 | 9/2010 | Jafari et al. | |
| 2010/0242961 A1 | 9/2010 | Mougel et al. | |
| 2010/0282259 A1 | 11/2010 | Figueiredo et al. | |

(56) References Cited

U.S. PATENT DOCUMENTS

| | | |
|---|---|---|
| 2010/0288283 A1 | 11/2010 | Campbell et al. |
| 2010/0292544 A1 | 11/2010 | Sherman et al. |
| 2010/0300446 A1 | 12/2010 | Nicolazzi et al. |
| 2010/0331639 A1 | 12/2010 | O'Reilly |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |

OTHER PUBLICATIONS

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

* cited by examiner

METHOD FOR VENTILATION

RELATED APPLICATION

This application claims the benefit of U.S. Provisional Application No. 61/235,588, filed Aug. 20, 2009, which application is hereby incorporated by reference.

BACKGROUND

Since the introduction of the microprocessor to mechanical ventilation systems, the industry has produced a potentially confusing plethora of options for breath modes, breath types and other therapies. The growth of applications has, to some extent, been fueled by competition between manufacturers and the result is a collection of critical care ventilators that attempt to be all things to all users. Lost in this are the occasional practitioners who are not experts in all the varied approaches and who work only infrequently with a ventilator. These users can be put off by the complexity of the user interface and may not be knowledgeable enough to select the appropriate therapy for a given subject. For instance, a severe flu epidemic or nerve gas terrorist attack might mean deploying large numbers of ventilators in the hands of minimally trained first responders.

In view of the importance of being capable of providing mechanical ventilation to a large number of subjects with minimal clinician support during an emergency, there is a need for a method of automatic control of a mechanical ventilator that may require the entering of a single subject physical characteristic for initiating mechanical ventilation on a subject, automatically managing said subject's mechanical ventilation, transitioning a mechanical ventilator to subject controlled ventilation, and weaning said subject from mechanical ventilation.

SUMMARY

This disclosure describes a method for automatically initiating ventilation, controlling ventilation, transitioning a ventilator to subject controlled ventilation, and weaning a subject from ventilation.

As discussed in greater detail below, the disclosure describes a method for automatically initiating ventilation that includes inputting a physical characteristic of the subject into a ventilator. The physical characteristic is preferably a characteristic correlating to the size or lung capacity of the subject, such as ideal body weight (IBW), height, or age. Based on the inputted physical characteristic, one or more ventilation parameters are calculated, such as duration of inspiration phase of breath ($T_{INSP}$), volume size of breath delivered to subject ($V_T$) or breathing frequency.

According to one embodiment, where the ventilation mode is a volume/assist mode and the inputted physical characteristic is ideal body weight, $T_{INSP}$ is calculated as a linear function of IBW; $V_T$ is also represented as a linear function of IBW; and breath frequency is determined using a preset $T_{INSP}:T_{EXP}$ ratio. If the ventilation mode is a Volume Targeted/Pressure Control mode (VTPC), $T_{INSP}$ is a linear function of IBW; inspiratory flow is based on predetermined $T_{RISE}$; and the target pressure is selected to achieve a pre-defined volume target expressed as a volume per unit of IBW.

Ventilation is initiated based on the calculated parameters. During ventilation at least one physiological parameter of the subject is monitored using one or more sensors. The physiological parameters may include positive airway pressure (PAP), lung flow (LF), arterial oxygen saturation ($S_PO_2$), pulse rate, end tidal exhaled carbon dioxide concentration ($E_TCO_2$), patient initiated breath rate, exhaled minute volume, and minute carbon dioxide production. At least one ventilation parameter may be adjusted based on the monitoring of the physiological parameters and the inputted physical characteristic.

In another embodiment, a method for automatically controlling ventilation of a subject who is initiating breathing efforts in a VTPC mode is disclosed. According to this embodiment, the PAP of the subject is measured. The first derivative of the PAP measurement is then calculated. If the first derivative approaches zero during the inspiratory time in VCV before the pressure target is reached and if the pattern is repetitive, at least one of $T_{RISE}$ or $T_{INSP}$ is adjusted such that the derivative of the pressure-time waveform has no more than one inflection point.

In a further embodiment, a method for automatically controlling ventilation of a subject is disclosed. According to this embodiment, an upper and lower bound of $E_TCO_2$ is set. The $E_TCO_2$ level of the subject is then measured. If the measured $E_TCO_2$ level of the subject exceeds the upper bound, at least one ventilator parameter is adjusted to reduce the $E_TCO_2$ level of the subject. The ventilator parameter may be breath volume (V) or breath frequency. In one embodiment, if the $E_TCO_2$ level exceeds the upper bound, the breath frequency parameter is adjusted. Additionally, the maximum PAP may be measured. If the maximum PAP is determined to be within a predetermined range of the upper bound, and if the $E_TCO_2$ level is too low, the breath volume parameter is adjusted.

In an additional embodiment, a method for automatically controlling ventilation of a subject is disclosed. According to this embodiment, an $S_PO_2$ target value is set. The $S_PO_2$ level of a subject is measured. If the measured $S_PO_2$ value of the subject is above or below the target value, the level of oxygen in the gas mixture is adjusted to achieve the $SpO_2$ target value. If the level of oxygen required to achieve the $S_PO_2$ target value exceeds a predetermined threshold for oxygen in the gas mixture, at least one of PEEP and $FiO_2$ is adjusted.

In another embodiment, a method for automatically transitioning a ventilator to subject control is disclosed. According to this embodiment, it is first determined whether the subject is attempting to initiate breaths. If a subject is not attempting to initiate breaths, the $E_TCO_2$ level of the subject is measured and compared to a pre-defined range. If the measured $E_TCO_2$ is within the range, the breath frequency is reduced after which the breath frequency is re-determined if the subject is initiating breaths. If the subject is attempting to initiate breaths for at least a predetermined percentage of the delivered breaths, the ventilator is switched to an assist mode whereby the ventilator delivered breaths are suspended.

In an additional embodiment, a method for automatically weaning a subject from a ventilator volume support mode is disclosed. At least one of $E_TCO_2$, $V_T$ and breath frequency is measured and compared with predetermined target ranges. If one or more measurements are within their target ranges for a predetermined period of time, and if the settings for $F_IO_2$ and PEEP are below pre-defined threshold values, then the ventilator is transitioned to a weaning mode. The ventilator is transitioned from a volume support mode to a pressure support mode by adjusting the pressure by a preset value below the target pressure utilized in the volume support mode. The pressure may be reduced in a step wise manner at predetermined intervals. A spontaneous breath trial may then be initiated. If it is determined that the subject can be removed from mechanical ventilation, an alert is provided.

These and various other features as well as advantages which characterize the disclosed systems and methods will be apparent from a reading of the following detailed description and a review of the associated drawings. Additional features of the device and methods described herein are set forth in the description which follows, and in part will be apparent from the description, or may be learned by practice of the technology. The benefits and features will be realized and attained by the structure particularly pointed out in the written description and claims as well as the appended drawings.

It is to be understood that both the foregoing general description and the following detailed description are exemplary and explanatory and are intended to provide further explanation of the disclosed technology as claimed.

BRIEF DESCRIPTION OF THE DRAWINGS

The following drawing figures, which form a part of this application, are illustrative of disclosed technology and are not meant to limit the scope of the description in any manner, which scope shall be based on the claims appended hereto.

DETAILED DESCRIPTION

This disclosure describes various methods for automatic mechanical ventilation. As will be discussed, the disclosure describes a method for automatically initiating mechanical ventilation, controlling mechanical ventilation, transitioning a mechanical ventilator to subject controlled ventilation, and weaning a subject from mechanical ventilation.

Initiation Phase

Figure 1:
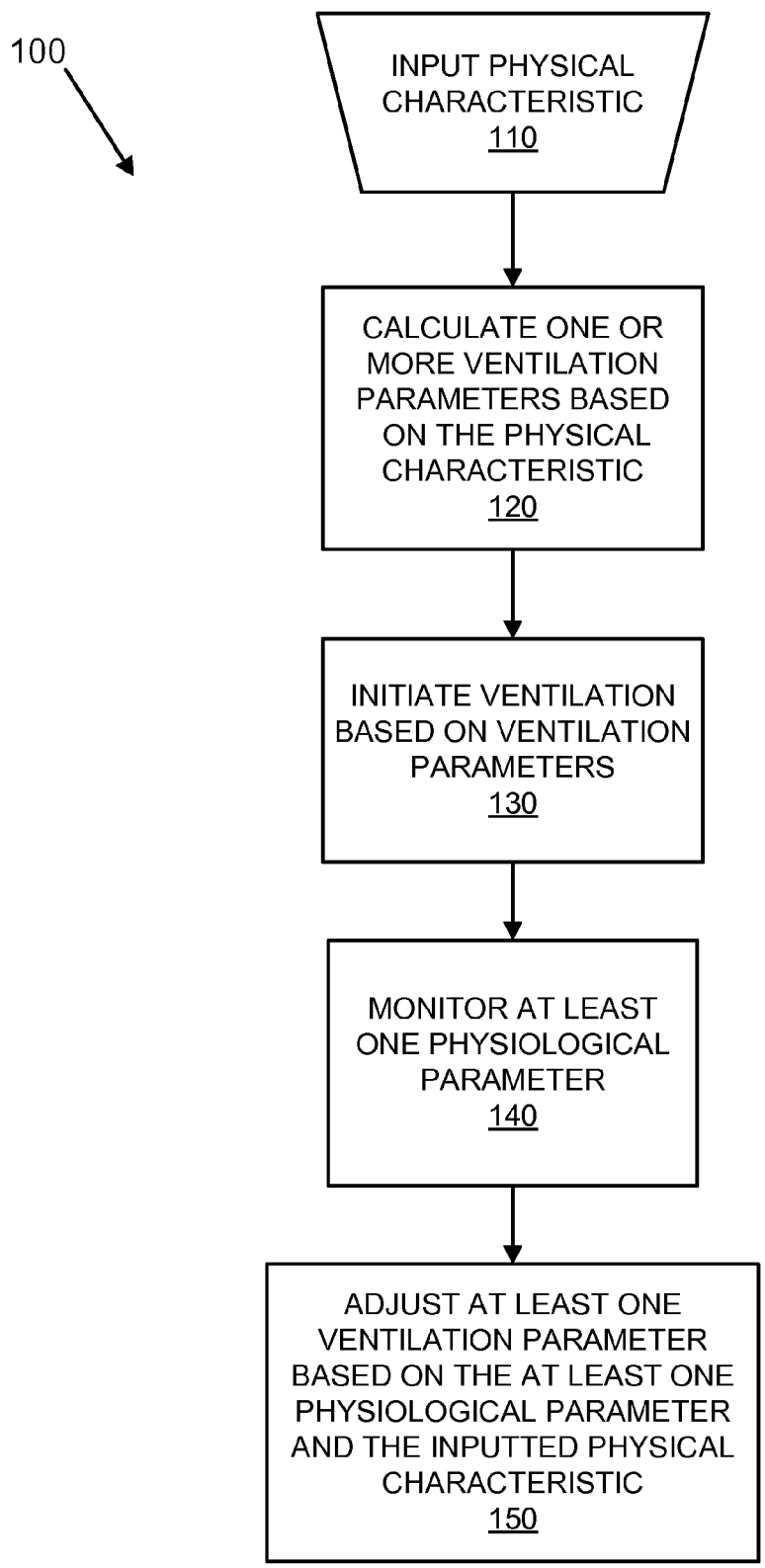
FIG. 1 illustrates a method for automatically initiating and adjusting mechanical ventilation.

FIG. 1 is a flow chart illustrating a method 100 for automatically initiating and adjusting mechanical ventilation in a subject.

According to an embodiment, step 110 inputs a physical characteristic. The physical characteristic may be any physical characteristic of a subject suitable for determining a ventilation parameter. In one embodiment, the physical characteristic is at least one of height, weight, ideal body weight, or age.

Step 120 calculates one or more ventilation parameters based on the physical characteristic. Suitable ventilation parameters include Fraction of Inspired Oxygen ($F_iO_2$), Inspiratory Time ($T_{INSP}$), gas mixture and breath frequency. Other suitable parameters include Positive End Expiratory Pressure (PEEP), Trigger Sensitivity, Tidal Volume ($V_T$), Inspiratory Flow, Plateau Time ($T_{PL}$), Inspiratory Pressure ($P_I$), Pressure Support ($P_{SUPP}$), Expiratory Sensitivity ($E_{SENS}$), Apnea Interval ($T_A$), Disconnect Sensitivity ($D_{SENS}$), Support Tube Compensation (TC %), Control percentage of work performed by Ventilator (PAV %), Sigh rate, and Sigh volume. This list is not restrictive. Any ventilation parameter capable of being calculated based on an inputted physical characteristic may be utilized without departing from the scope and intent of the disclosure.

Accordingly, Step 130 initiates ventilation based on the calculated ventilation parameters. Step 140 monitors at least one physiological parameter of the subject. The physiological parameter may include positive airway pressure (PAP), lung flow (LF), arterial oxygen saturation (SpO2), pulse rate, end tidal exhaled carbon dioxide concentrations ($E_TCO_2$), patient initiated breath rate, exhaled minute volume, and minute carbon dioxide production. This list is not restrictive. Step 150 adjusts at least one ventilation parameter based on the inputted physical characteristic and the monitoring of the physiological parameter.

Figure 2:
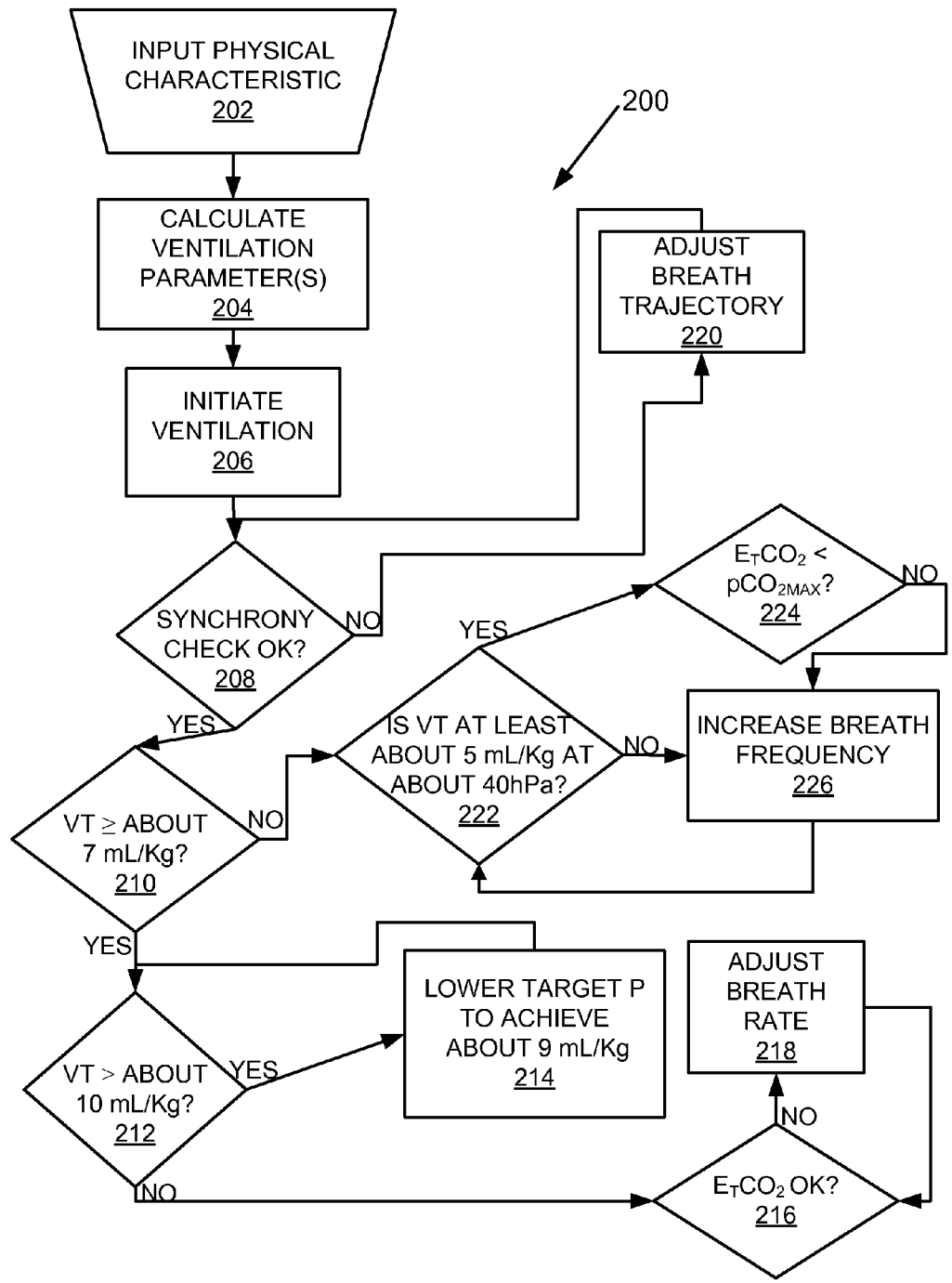
FIG. 2 illustrates a method for automatically initiating and adjusting mechanical ventilation.

FIG. 2 is a flow chart illustrating a method 200 for automatically initiating and adjusting mechanical ventilation in a subject.

According to an embodiment, step 202 inputs a physical characteristic. Step 204 calculates one or more ventilation parameters based on the physical characteristic. Accordingly, Step 206 initiates mechanical ventilation based on the calculated ventilation parameter(s).

Step 208 determines if ventilation is substantially synchronized with the breathing efforts of the subject. In one embodiment, this is determined by analyzing the first time derivative of the positive pressure signal. As used herein, all "predetermined" levels, boundaries, maximums, minimums or ranges are standard for every subject, inputted, or calculated based on an inputted physical characteristic. If Step 208 determines that ventilation of the subject is not substantially synchronized with the breathing efforts of the subject, Step 220 adjusts the breath trajectory. If Step 208 determines that ventilation is substantially synchronized with the breathing efforts of the subject, Step 210 determines if the Volume Target (VT) is equal to or greater than a desired amount, such as about 7 ml/kg. If step 210 determines that the volume target is not equal to or greater than about 7 ml/kg, Step 222 determines if the volume target is at least about 5 ml/kg at about 40 hPa. If Step 222 determines that the volume target is at least about 5 ml/kg at about 40 hPa, Step 224 determines if the $E_TCO_2$ level of the subject is less than a predetermined maximum partial pressure of carbon dioxide ($pCO_{2MAX}$). $pCO_{2MAX}$ may be a predetermined boundary. If Step 224 determines that the $E_TCO_2$ is not less than the $pCO_{2MAX}$, Step 226 increases the breath frequency. In one embodiment, the increase in breath frequency reduces the $E_TCO_2$ level of the subject to a target value. If Step 210 determines that volume target is greater than or equal to about 7 ml/kg, Step 212 determines if the volume target is greater than about 10 ml/kg. If Step 212 determines that the volume target is greater than about 10 ml/kg, Step 214 lowers the target Pressure (P) to achieve a volume target of about 9 ml/kg. In one embodiment, Step 214 lowers the target Pressure (P) to achieve a volume target of about 9 ml/kg based on the subject's dynamic compliance (CDYN). If Step 212 determines that the volume target is not greater than or equal to about 10 ml/kg, Step 216 determines if the $E_TCO_2$ level of the subject is within a predetermined range. In one embodiment, the predetermined $E_TCO_2$ level may range from a target $E_TCO_2$ with a variance of plus or minus 2 Torr (+/−2 Torr). If step 216 determines that the $E_TCO_2$ level of the subject is within the predetermined alert range, alert limits are set. If Step 216 determines that the $E_TCO_2$ level of the subject is not within a predetermined range, Step 218 adjusts the breath rate.

In a further embodiment, the ventilator initiates Volume Assist/Control Ventilation by calculating an appropriate duration for the inspiration phase of the breath ($T_{INSP}$). In one embodiment, of this approach, the duration is a linear function of the subject's ideal body weight (IBW). One particular solution uses the function: $\{T_{INSP}=400+5\times IBW\}$ where the time is in milliseconds and IBW is in kilograms. In another embodiment, the scalar in the equation above (i.e. 5 in the equation above) may range from about 4 to 8. In a further embodiment, the base value in the equation above (i.e. 400 in the equation above) may range from about 300 to 500. Next, the appropriate average flow rate of breathing gas delivered during the inspiration phase of breathing is calculated. The flow is computed such that the volume of breathing gas delivered during the inspiration phase is a linear function of the IBW. The flow is calculated with the following equation: $V_T=(0.007\times \text{ideal body weight}\times 60)T_{INSP}$. In another embodiment, the equation above may include a base value (i.e. 0.007 in the equation above) of about 0.0005 to 0.001. The initial frequency at which the breaths are delivered are calculated by using a defined ratio of inspiration time to exhalation time or a defined breath frequency ($T_{INSP}:T_{EXP}$). In one embodiment, this ratio is about 1:3. In another embodiment, this ratio may from about 1:2 to 1:4.

Alternatively, in another embodiment, the ventilator initiates Volume Targeted, Pressure Control Ventilation (VTPC). In this embodiment, the ventilator delivers a series of test breaths using an inflation pressure of about 10 to 40 hPa. In another embodiment, the ventilator delivers a series of test breaths using an inflation pressure of about 10 to 20 hPa. $T_{INSP}$ is a linear function of the subject's IBW. In one embodiment, the linear function is: $\{T_{INSP}=400+5\times IBW\}$ where the time is in milliseconds and IBW is in kilograms. In another embodiment, the scalar in the equation above (i.e. 5 in the equation above) may range from about 4 to 8. In a further embodiment, the base value in the equation above (i.e. 400 in the equation above) may be range from about 300 to 500. The rate at which the breathing gas is delivered is based upon a rise time of about 40 to 60% (e.g. the gas volume is modulated such that the pressure target will be reached in ½ the $T_{INSP}$). Based upon the data collected and/or information learned during the test breaths, the delivery pressure target may be selected to achieve a pre-defined volume target. In one embodiment, this target is about 5 to 10 ml/kg IBW. In another embodiment, this target is about 7 ml/kg IBW. In one embodiment, the amount of volume delivered per unit pressure is monitored during the test breaths.

In this embodiment, where the ventilator delivers a series of breaths, an algorithm measures the volume delivered at the initial pressure and then computes the pressure needed to deliver a target volume. This is an iterative process that may take several breaths to achieve a targeted volume even after pressure is adjusted on a breath-to-breath basis.

Also, according to this embodiment, the breathing gas mix delivered to the subject may be initiated at about 100% oxygen and is automatically adjusted based upon the monitored parameters of the subject. The ventilator may also apply an initial level of Positive End Expiratory Pressure (PEEP), which may be adjusted automatically based upon the monitored parameters of the subject.

In one embodiment, when the physical characteristic is subject size (i.e. IBW, height, or weight), the desired mixture of breathing gas is based upon the inputted physical characteristic. For instance, the mixture may be about 100% oxygen for subjects weighing more than about 10 kg and about 60% oxygen balanced with nitrogen for subjects weighing about 10 kg or less.

In another embodiment, the initial setting for Positive End Expiratory Pressure (PEEP) is based upon an inputted physical characteristic. For instance, where the inputted characteristic is IBW, the setting may be about 3 centimeters of water pressure for subjects weighing about 10 kg or less and about 5 centimeters of water pressure for subjects weighing more than about 10 kg. In a particular embodiment, PEEP will be initialized at about 4 hPa for all subjects.

Figure 14:
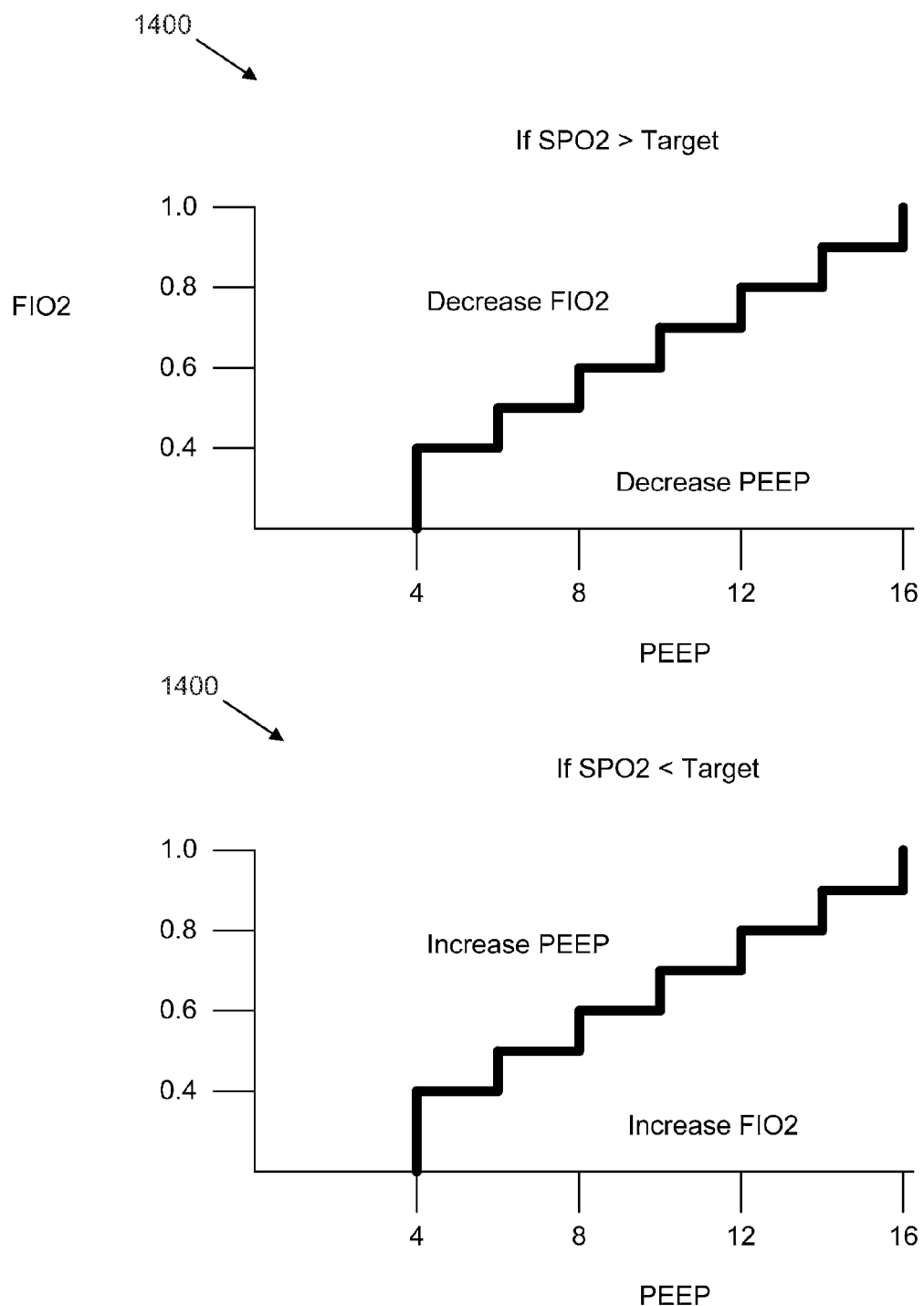
FIG. 14 illustrates a graph of arbiter functions.

In a further embodiment, both PEEP and $F_IO_2$ may be calculated to achieve a predetermined target for $S_PO_2$. Both PEEP and $F_IO_2$ may be calculated based upon an inputted physical characteristic. In one embodiment, these inputs include $S_PO_2$, pulse rate, minute ventilation and breathing frequency. The ventilator may use an arbiter function to determine whether to adjust PEEP, $F_IO_2$ or both simultaneously. FIG. 14 is a graph illustrating arbiter functions 1400. In one embodiment, the arbiter utilizes the functions 1400 illustrated in FIG. 14.

In an additional embodiment, methods 100 and 200 for automatically initiating and adjusting ventilation in a subject may further include the production of an alert. If any of the physiological parameters exceed a predetermined range an alert may be produced.

Management Phase

Once ventilation is initiated, it should be determined whether or not the subject is initiating any breathing efforts. If yes, the PAP and LF signals may be analyzed to determine if the ventilator's delivery of breathing gas is consistent with meeting the demand of the subject.

Figure 3:
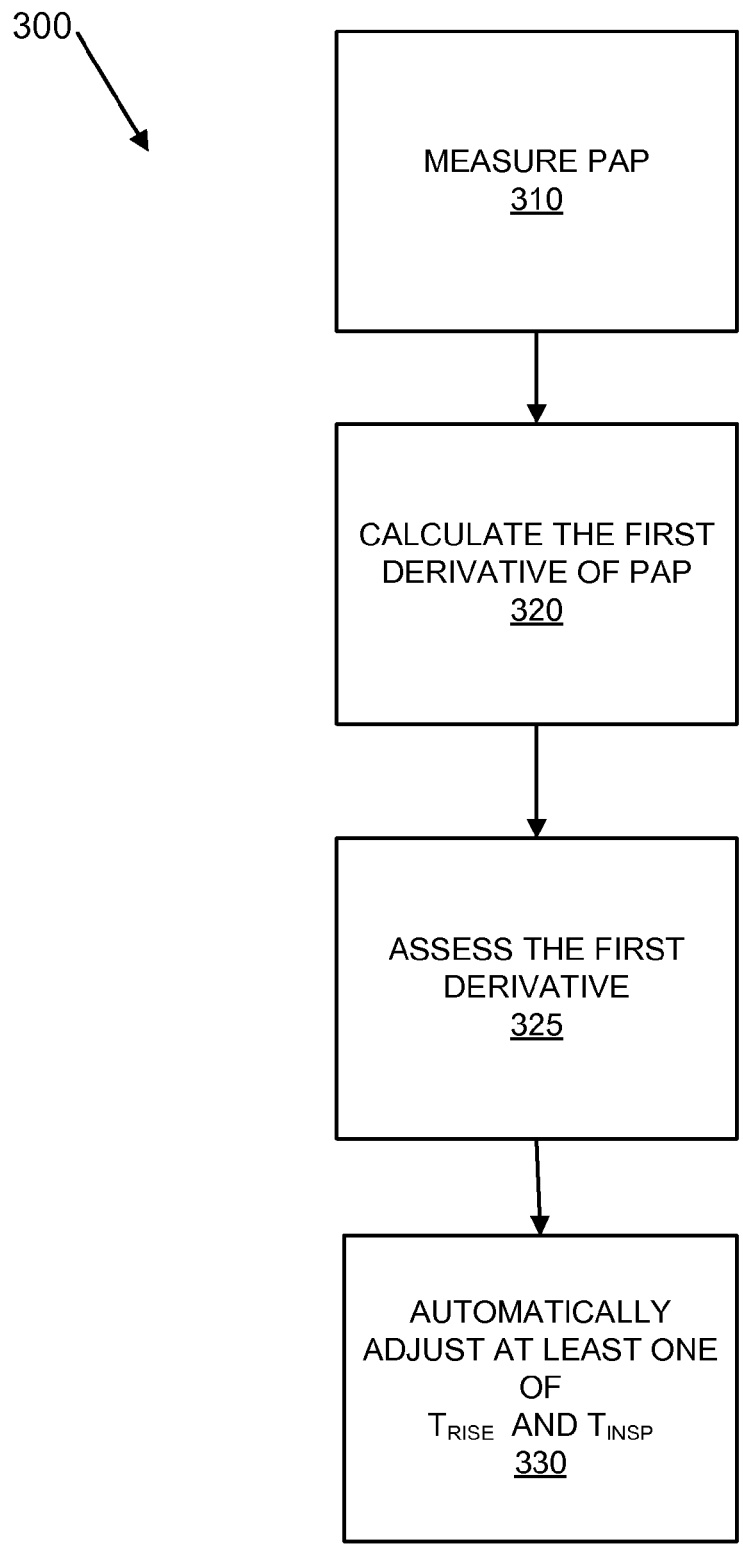
FIG. 3 illustrates a method for automatically controlling mechanical ventilation of a subject initiating breathing efforts.

FIG. 3 is a flow chart illustrating a method 300 for automatically controlling mechanical ventilation of a subject initiating breathing efforts.

According to an embodiment, step 310 measures PAP, after which Step 320 calculates the first derivative of the PAP measurement. In one embodiment, method 300 is in a VTPC mode. In some embodiments, the first derivative of the PAP measurement may be determined in accordance with the methods disclosed in U.S. patent application Ser. No. 12/479, 230, filed Jun. 5, 2009, and entitled *Systems and Methods for Determining Patient Effort and/or Respiratory Parameters in a Ventilation System*, the complete disclosure of which is incorporated herein by reference.

Step 325 assesses the first derivative. If Step 325 determines that the first derivative approaches zero (or some other limit approaching zero) during the inspiratory time in VCV before the pressure target is reached, and if a pattern is repetitive (e.g., an algorithm will determine whether it exists on a majority of the breaths), Step 330 automatically adjusts at least one of $T_{RISE}$ and $T_{INSP}$ such that the derivative of the pressure-time waveform has no more than one inflection point.

In one embodiment, if there is an early inflection point (dP/dt approaches zero during the rising segment of the pressure waveform) and the ventilator mode is VTPC, the rise time will change by 10% to achieve the pressure target. If the inflection occurs after target pressure is reached (dP/dt goes negative then positive) then the inspiratory time is decreased to terminate the breath prior to the time the inflection occurs. In another embodiment, the breath is terminated about 50 ms earlier than the average occurrence of the negative inflection.

In further embodiment, if the mode is VCV, and the pressure waveform has an inflection point anytime during $T_{INSP}$, the algorithm will increase the flow rate in fixed increments. In one embodiment, the increments will be about 10% of the current value.

If the Volume Target/Pressure Control (VTPC) approach is utilized in this embodiment, Step 330 will automatically adjust $T_{RISE}$. In an alternative embodiment, if the second derivative of the PAP signal becomes positive at any time after the first ½ of the inspiration phase, the inspiration phase will be adjusted to terminate. In either case, the delivery of breathing gas may be automatically adjusted to achieve the same volume during the modified inspiration phase.

In another embodiment, after initiation, the adequacy of ventilation shall be determined. This may be accomplished by monitoring parameters of the subject, such as $E_TCO_2$.

Figure 4:
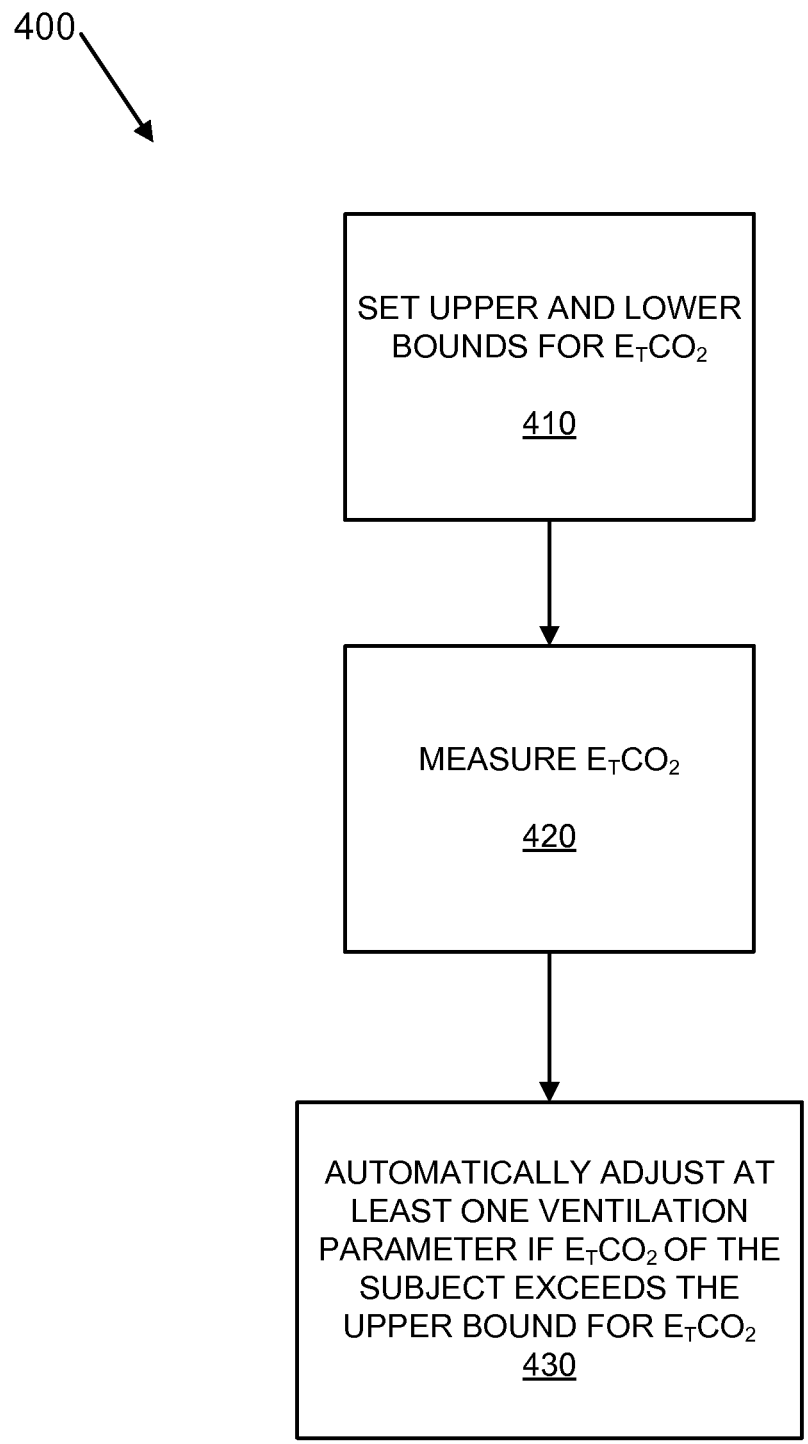
FIG. 4 illustrates a method for automatically controlling mechanical ventilation of a subject.
Figure 5:
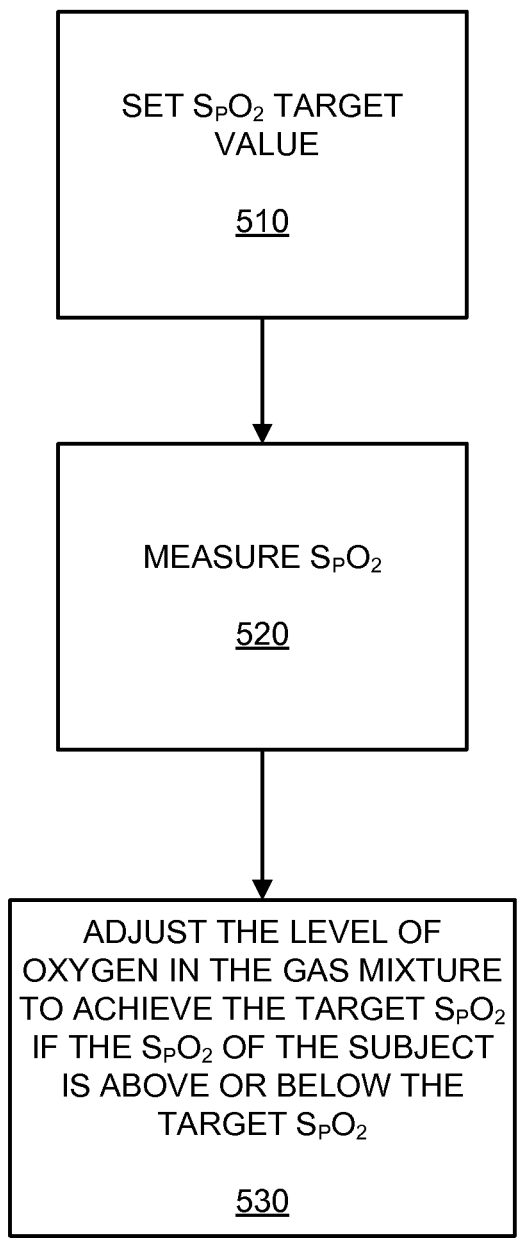
FIG. 5 illustrates a method for automatically controlling mechanical ventilation of a subject.

FIG. 4 is a flow chart illustrating a method 400 for automatically controlling mechanical ventilation of a subject.

According to an embodiment, step 410 sets an upper and lower bound for $E_TCO_2$. Step 420 measures $E_TCO_2$ of the subject. If the $E_TCO_2$ of the subject exceeds the set upper bound, Step 430 automatically adjusts at least one ventilator parameter. In one embodiment, the level of ventilation of the subject's lungs will be adjusted proportionately, to attempt to bring the $E_TCO_2$ back into the desired range. In another embodiment, the lower bound may be about 40 Torr and the upper bound may be about 45 Torr. In one embodiment, the ventilator parameter is breath volume ($V_T$). In another embodiment, the ventilation parameter is breath frequency.

In an alternative embodiment, if a subject is initiating a breath and the $E_TCO_2$ of the subject exceeds the set upper bound for $E_TCO_2$ the level of ventilation of the subject's lungs will be adjusted proportionately, to attempt to bring the $E_TCO_2$ back into the desired range. In another embodiment, if $E_TCO_2$ is below a set lower bound, an alert will be generated. The alert may be an audible and/or visual indicator, which may operate to inform a user or caregiver of this or another patient and/or system condition.

In either case, the adjustment may be to breath frequency (in order to avoid possible changes to the ratio of ventilation dead space to tidal volume).

In another embodiment, the PAP signal is assessed. If the maximum PAP value is within predetermined bounds, the volume delivered per breath will be changed. If further change is required, the frequency will be adjusted. In either case, the percent change to the minute ventilation may be a (linear) function of the desired percent change to the $E_TCO_2$.

Coincident with the assessment of ventilation, the subject's oxygenation may be assessed.

FIG, 5 is a flow chart illustrating a method 500 for automatically controlling mechanical ventilation of a subject.

According to an embodiment, Step 510 sets a $S_PO_2$ target value. The $S_PO_2$ target value may be a predetermined range of acceptable $S_PO_2$ levels. In one embodiment, the $S_PO_2$ target may be set to a value between about 86 and 98 percent. In one embodiment, the target may be about 94%. Step 520 measures the $S_PO_2$ of the subject. Provided the $S_PO_2$ input is valid, the mix of the breathing gas may be adjusted periodically according to a difference formula wherein the level of oxygen in the mix may be changed by some amount depending on whether the $S_PO_2$ reading is higher or lower than the target value. If the $S_PO_2$ of the subject is above or below the $S_PO_2$ target value, Step 530 adjusts the level of oxygen in the gas mixture to achieve the $S_PO_2$ target value. In one embodiment, the adjustment might be a percentage change proportional to the desired change in $S_PO_2$. For instance, in one embodiment, if the $S_PO_2$ is below target by about 4%, the delivered oxygen percentage would be increased by about 4%.

In a second embodiment, the ventilator might change the oxygen level in the gas mix to achieve a desired change in alveolar oxygen concentration ($F_AO_2$) via an algorithm using the computed alveolar-arterial oxygen tension difference and the normal oxyhemoglobin dissociation curve. In one embodiment, the algorithm calculates the alveolar $P_AO_2$ that corresponds to the measured $S_PO_2$ to compute the alveolar-arterial oxygen tension difference. The algorithm may then calculate the $P_AO_2$ required to achieve the target $S_PO_2$ based on the alveolar-arterial oxygen tension difference.

In one embodiment, the changes to the breathing mix may occur at predetermined intervals which might be different for increases and decreases in delivered oxygen concentration. In a specific embodiment, the interval will be between about 30 seconds and 5 minutes. In an alternative embodiment, the interval will be between about 30 seconds and 3 minutes.

In the event the level of delivered oxygen in the mix required to achieve the target $S_PO_2$ is greater than a predetermined level, the ventilator shall automatically increase the level of PEEP. The level of PEEP may be changed by predetermined increments or the change may be based upon the determination of inflection points in the pressure volume plots averaged over several breaths. In one embodiment, the change will be an increment of about 1 to 2 centimeters of water pressure. In this embodiment, an upper limit is defined for both weight categories beyond which PEEP shall no longer be incremented. The algorithm may have a predetermined interval for changes. In general, this interval may be longer than the $F_IO_2$ change interval. In one embodiment, the interval may be about 30 minutes. In another embodiment, the interval may range from about 5 to 30 minutes.

In another embodiment, a predetermined $F_IO_2$ value or set of predetermined $F_IO_2$ values is used as the basis for modifying PEEP. For instance, the PEEP controller may down regulate the PEEP level if the $F_IO_2$ is less than about 30% to 40%. The down-regulation may be in increments and may be limited by monitoring subject parameters related to oxygenation and lung mechanics.

In one embodiment, $S_PO_2$ may be evaluated in the period following the decrease in PEEP. Provided the $S_PO_2$ input is valid, if the $S_PO_2$ drops by more than a predetermined amount, the PEEP may be reinstated to the preceding value.

Figure 6:
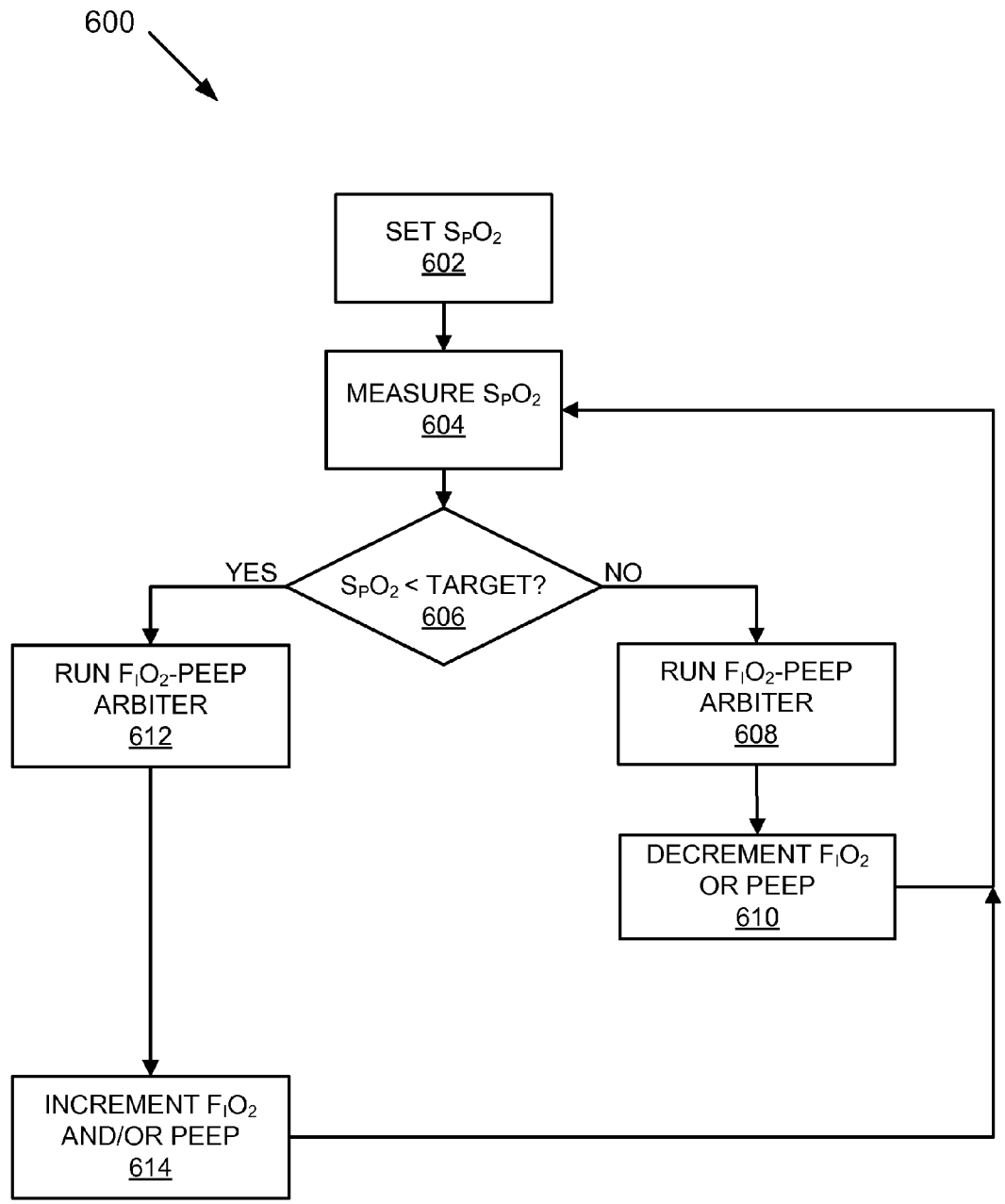
FIG. 6 illustrates a method for automatically controlling mechanical ventilation of a subject.

FIG. 6 is a flow chart illustrating a method 600 for automatically controlling mechanical ventilation of a subject.

According to an embodiment, step 602 sets a $S_PO_2$ target value. Step 604 measures $S_PO_2$ of a subject. Step 606 determines if the $S_PO_2$ of the subject is lower than the $S_PO_2$ target. If Step 606 determines that the $S_PO_2$ of the subject is higher than or equal to the $S_PO_2$ target and the $S_PO_2$ input is valid, step 608 runs an $F_IO_2$-PEEP arbiter. In one embodiment, the arbiter may utilize the arbiter functions 1400 illustrated in FIG. 14. Next, Step 610 adjusts at least one of PEEP and/or $F_IO_2$ in decrements, after which step 604 may be repeated. If Step 606 determines that the $S_PO_2$ of the subject is lower than the $S_PO_2$ target, step 612 runs an $F_IO_2$-PEEP arbiter. Next, Step 614 adjusts at least one of PEEP and/or $F_IO_2$ in increments, after which step 604 may be repeated.

In an alternative embodiment, after step 612, the ventilator may determine if a change in PEEP is indicated. If a change in PEEP is indicated, PEEP may be adjusted in increments.

After adjusting PEEP, the ventilator may determine if Peak Inspiration Pressure (PIP) changed by more than PEEP. If PIP changed by more than PEEP, $F_iO_2$ is adjusted in increments after which the $S_pO_2$ of the subject is remeasured. If a change is PEEP is not indicated, the $S_pO_2$ of a subject remeasured.

In a further embodiment, an alert may be provided if the $F_iO_2$, PEEP, or $S_pO_2$ of the subject are outside of predetermined ranges.

Transitioning to Subject Control Phase

The ventilator may continuously assess the ability of the subject to initiate breaths. In the event that no initiations are detected, and the $E_TCO_2$ is within a pre-defined range, the ventilator will periodically reduce the breath delivery frequency for a time in order to stimulate the subject to breathe. In one embodiment, the period of time will be about every 30 minutes to 60 minutes and the duration may be about 3 to 5 minutes. In an alternative embodiment, the period of time will be greater than 60 minutes. In one embodiment, the period of time will be about 30 minutes.

Figure 7:
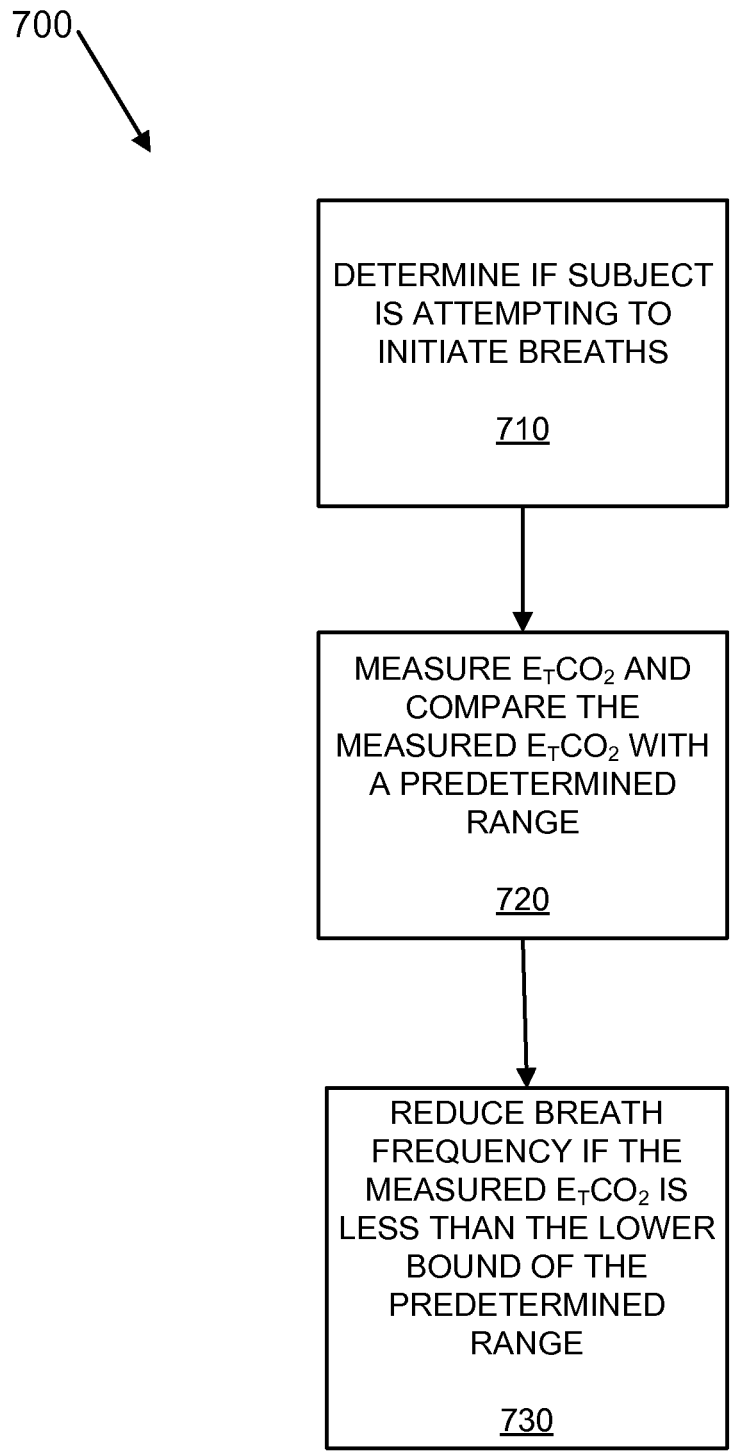
FIG. 7 illustrates a method for automatically transitioning a mechanical ventilator to subject control.

FIG. 7 is a flow chart illustrating a method 700 for automatically transitioning a mechanical ventilator to subject control.

According to an embodiment, step 710 determines if a subject is attempting to initiate breaths. If Step 710 determines that the subject is attempting to initiate breaths, step 720 measures the $E_TCO_2$ of the subject and compares the measured $E_TCO_2$ with a predetermined $E_TCO_2$. If Step 710 determines that the measured $E_TCO_2$ is less than the lower bound of the predetermined $E_TCO_2$ range for a predetermined period of time, Step 730 reduces breath frequency.

In an alternative embodiment, step 710 determines if a subject is attempting to initiate breaths. If Step 710 determines that the subject is attempting to initiate breaths, a subject is periodically stimulated to breathe by reducing the breath rate, for example by about 10%.

In one embodiment, the reduction in breath frequency will be terminated if the $E_TCO_2$ exceeds some predetermined second limit, higher than the upper bound of the desired range.

In one embodiment, if the ventilator determines that the subject is attempting to initiate at least some minimum, predetermined fraction of the delivered breaths, the ventilator will suspend ventilator delivered breaths in favor of allowing the subject to operate the ventilator in an "assist" mode. In an embodiment, the assist mode comprises suspending ventilator initiated breaths as long as the subject continues to initiate breaths or until the measured $E_TCO_2$ is below a pre-determined level.

In another embodiment, if the subject demonstrates the ability to auto-regulate their own $E_TCO_2$ over a predetermined period, the ventilator may then transition ventilation to a Volume Support regime (VS). In one embodiment, the VS may utilize the most recent end-inspiration pressure level as the starting point for initiating VS. In another embodiment, the transition may be achieved by computing the pressure required to deliver the current breath volume based upon the subject's dynamic compliance. In a further embodiment, the transition may be achieved by calculating the pressure required to deliver the current breath volume and utilizing the calculated pressure as the starting pressure for Volume Support. In one embodiment, if the ventilator is transitioning from VCV, the $T_{RISE}$ may be set to a predetermined level. In one embodiment, this level may be about 50%. In one embodiment, the predetermined $T_{RISE}$ value may change from about 10 to 90% while determining if ventilation is substantially synchronized with the breathing efforts of the subject. In a further embodiment, the breath timing may be based upon flow deceleration such that the inspiration phase may be terminated once the lung flow drops to a predetermined percentage of the peak flow. In one embodiment, this percentage may be about 25%. In another embodiment, the predetermined lung flow value may change from about 10 to 90%, while determining if ventilation is substantially synchronized with the breathing efforts of the subject. As in the initiation stage, the settings may be assessed for subject comfort, based upon analysis of the PAP and LF signals as previously described. If necessary, in one embodiment, the $T_{RISE}$ and/or flow cycle values may be adjusted automatically to optimize the ventilator's response to subject effort.

Once the subject has successfully transitioned to spontaneous breathing in a Volume Support (VS) regime, the ventilator may monitor the subject for a minimum period of time. In one embodiment, the minimum period of time is about 30 minutes. In another embodiment, the period of time may be from about 30 minutes to about 4 hours. The response of the subject may be assessed by monitoring the $E_TCO_2$, the delivered volume, and the breath frequency. In one embodiment, data from other subject monitoring devices will allow for assessment of stability of other vital subject data. In another embodiment, each parameter has predetermined acceptance criteria and if the value (or the values of combined parameters derived from these values) remains in acceptable ranges for a defined period, the ventilator automatically transitions to a weaning stage. In one embodiment, the stability period is about 30 minutes and the acceptance criteria is an $E_TCO_2$ level of less than about 45 Torr, a Rapid Shallow Breathing Index of less than about 200 and a variability in pulse rate of less than a specified amount, such as about +/−25%. It will be appreciated by those skilled in the art that other values may be used for the stability period and acceptance criteria within the scope of the present disclosure.

Figure 8:
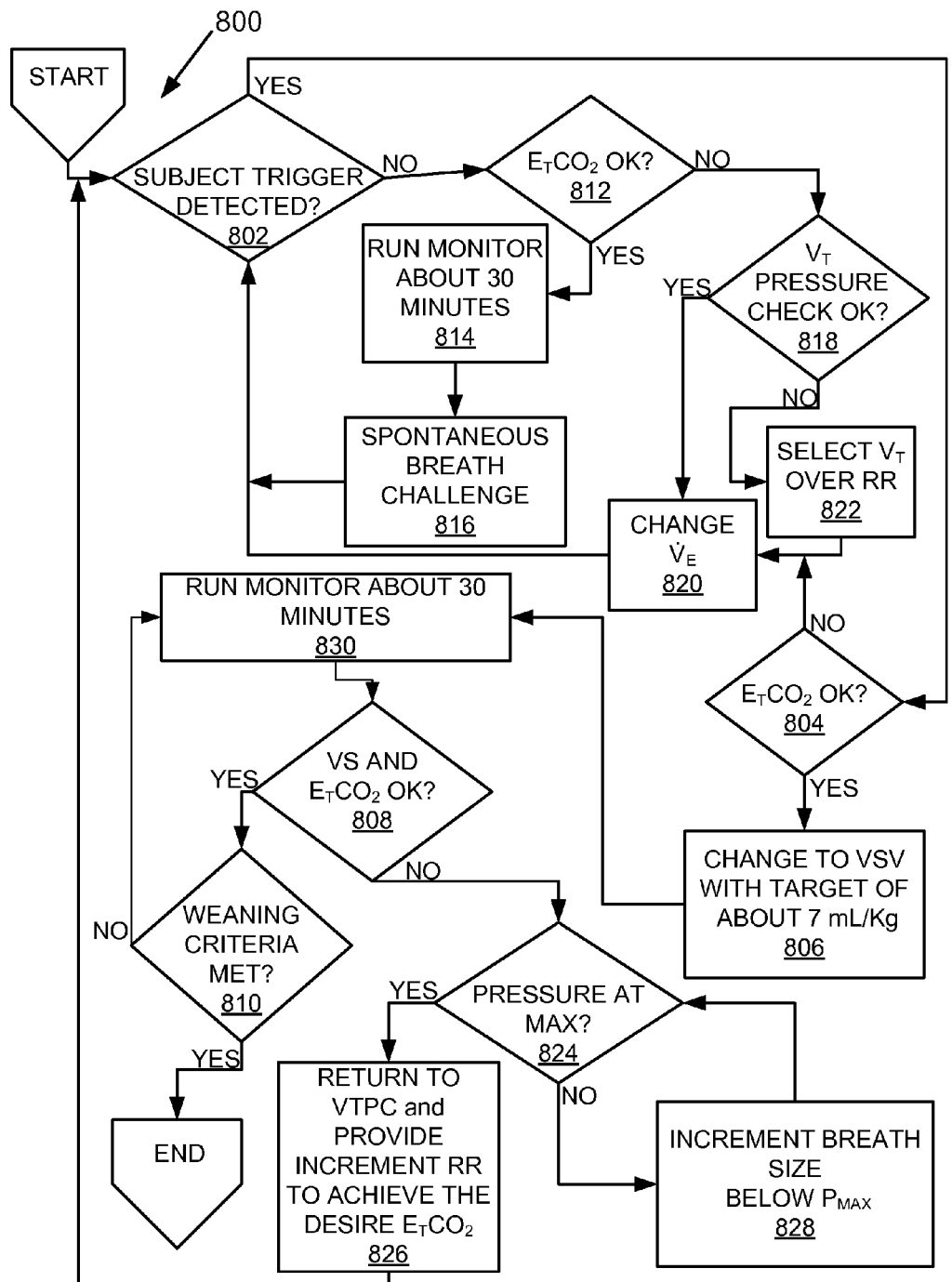
FIG. 8 illustrates a method for automatically transitioning a mechanical ventilator to subject control.

FIG. 8 is a flow chart illustrating a method 800 for automatically transitioning a mechanical ventilator to subject control.

According to an embodiment, Step 802 determines if a subject is attempting to initiate a predetermined percentage of delivered breaths. If Step 802 determines that the subject is attempting to initiate breaths, Step 804 determines if the $E_TCO_2$ of the subject is within an acceptable range. If Step 804 determines that the $E_TCO_2$ of the subject is within the acceptable range, Step 806 changes the ventilator to Volume Support Ventilation (VSV). The VSV may have a target of about 7 ml/kg. After Step 806, Step 830 runs a monitor for about 30 minutes. After Step 830, Step 808 determines if Volume Support (VS) and the $E_TCO_2$ of the subject are within the predetermined acceptable range. If Step 808 determines that the VS and the $E_TCO_2$ of the subject are within the predetermined acceptable ranges, Step 810 determines if the weaning criteria has been met. If Step 810 determines that the weaning criteria has been met, then the ventilator either automatically transitions the subject into a weaning ventilation mode or notifies a clinician that the subject is ready for a weaning ventilation mode. If Step 810 determines that the weaning criteria has not been met, Step 830 is repeated. If Step 802 determines that the subject is not attempting to initiate breaths, Step 812 determines if the $E_TCO_2$ of the subject is within a predetermined acceptable range. If Step 812 determines that the $E_TCO_2$ of the subject is within the predetermined acceptable range, Step 814 monitors the $E_TCO_2$ level for a predetermined period of time, such as about 30 minutes. Following Step 814, Step 816 initiates a spontaneous breath challenge (SBC), after which Step 802 may be repeated. If Step 812 determines that the $E_TCO_2$ level is not within the predetermined acceptable range, Step 818 determines if at least one of tidal volume ($V_T$) or pressure is within a predetermined acceptable range. If Step 818 determines that at least one of $V_T$ or pressure is within a predetermined acceptable range, Step 820 changes the Exhaled Minute Volume ($\dot{V}_E$). If Step 818 determines that at least one of $V_T$ or pressure is not within the predetermined acceptable range, Step 822 selects $V_T$ over Respiratory Rate (RR) after which Step 820 changes the $\dot{V}_E$. After step 820, Step 802 is repeated. If step 808 determines that the VS and $E_TCO_2$ are not within the predetermined acceptable ranges, then Step 824 determines if pressure is at $P_{MAX}$. If Step 824 determines that pressure is at $P_{MAX}$, Step 826 returns to VTPC and provides increment RR to achieve the desired $E_TCO_2$ after which step 802 may be repeated. If Step 826 determines that pressure is not at $P_{MAX}$, Step 828 provides incremented breath sizes below $P_{MAX}$ after which Step 830 is repeated.

Weaning Phase

The ventilator may enter the weaning phase either automatically, or upon user command.

Figure 9:
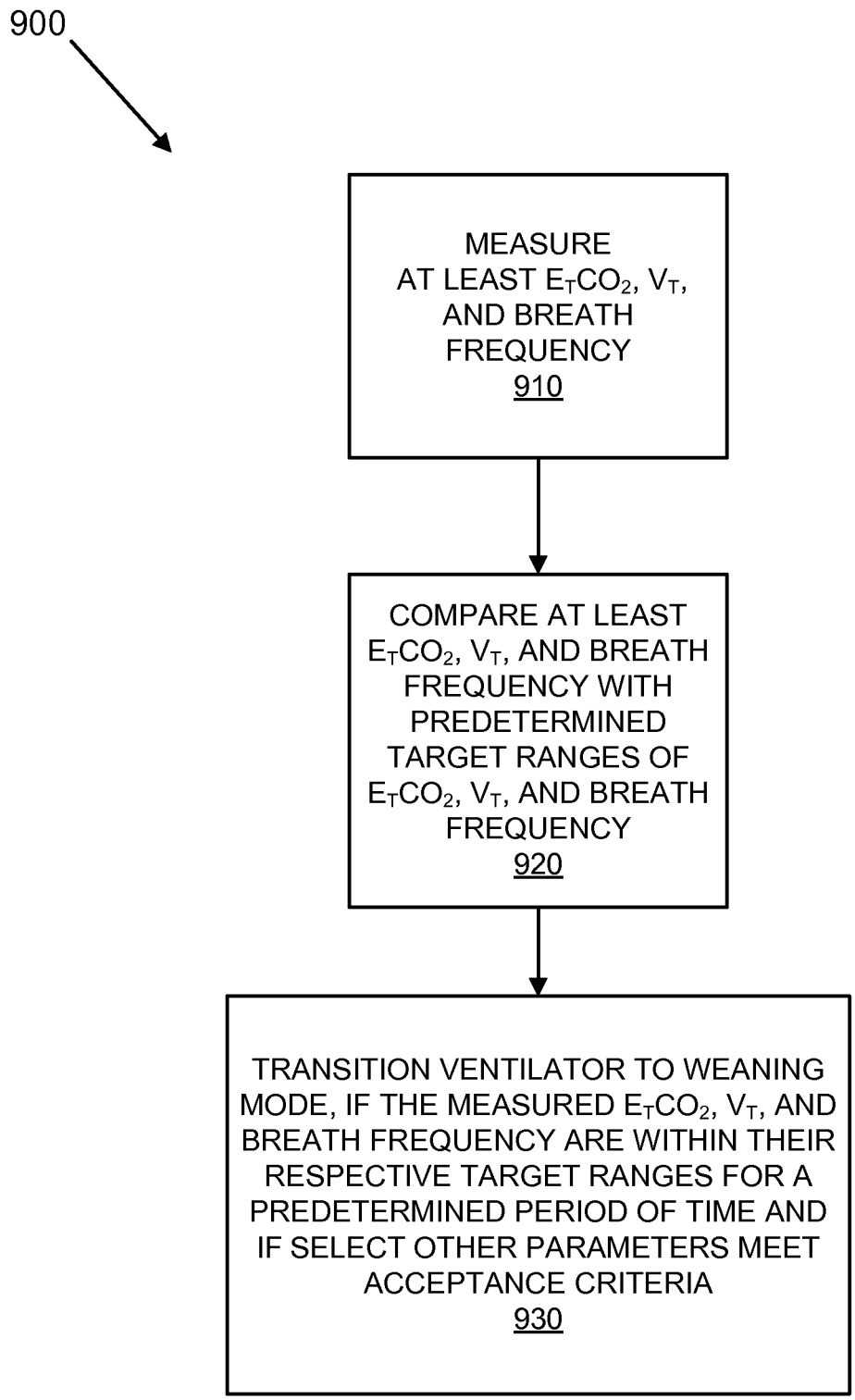
FIG. 9 illustrates a method for automatically weaning a subject from a mechanical ventilator in a volume support mode.

FIG. 9 is a flow chart illustrating a method 900 for automatically weaning a subject from a mechanical ventilator in volume support mode.

According to an embodiment, step 910 measures at least $E_TCO_2$, $V_T$, and breath frequency. Step 920 compares the measured $E_TCO_2$, $V_T$, and breath frequency with predetermined target ranges of $E_TCO_2$, $V_T$, and breath frequency. If the measured $E_TCO_2$, $V_T$, and breath frequency are within their respective ranges for a predetermined period of time and if select other parameters are within their acceptance criteria, Step 930 transitions ventilation to a weaning mode. In one embodiment, the select other parameters may be $F_IO_2$ and PEEP.

In one embodiment, the ventilator transitions to Pressure Support Ventilation with an initial pressure of about 2 hPa less than the target pressure used in Volume Support mode. In a further embodiment, subject monitoring evaluates a plurality of subject parameters during the control interval, and if the plurality of signals are within the acceptable ranges, the pressure support level will be reduced at the end of the control interval. In a further embodiment, when one or more parameters exceed acceptance limits, the controller may wait about three minutes. In one embodiment, the controller may wait for about 1 to 5 minutes. If the variable(s) are still out of range after the wait period, the pressure support level shall be increased. Decreases or increases of pressure support may be made in discreet steps or increments/decrements followed by an assessment period. In one embodiment, the step size is about 2 hPa and the assessment period is about 15 minutes. In one embodiment, if the PS level is going down, the potential assessment period is about 15 minutes to about 2 hours. In alternative embodiment, if the PS level is going up, the lower end of the range will be determined by the response of the subject. If the response is less than desired, the interval may be about 2 minutes. In another embodiment, the assessment period may be a function of subject size.

A minimal level of pressure support (which may be different for different sized subjects) may be defined. In one embodiment, once the subject has weaned to a Pressure Support minimum ($PS_{MIN}$), the ventilator may recommend a Spontaneous Breathing Trial (SBT) or, in another embodiment, automatically start a SBT. $PS_{MIN}$ may be a predetermined minimum boundary of pressure for supporting a subject in a pressure support ventilation mode. In a further embodiment, if, at any time during the weaning phase, the subject parameters indicate inability to ventilate, the ventilator reverts to VTPC and re-enters the control scheme at that point. In an alternative embodiment, if subject's physiologic parameters remain stable for a predetermined period on $PS_{MIN}$, the trial shall be deemed successful and an alert produced which may notify a clinician that the subject can be removed from mechanical ventilation.

Figure 10:
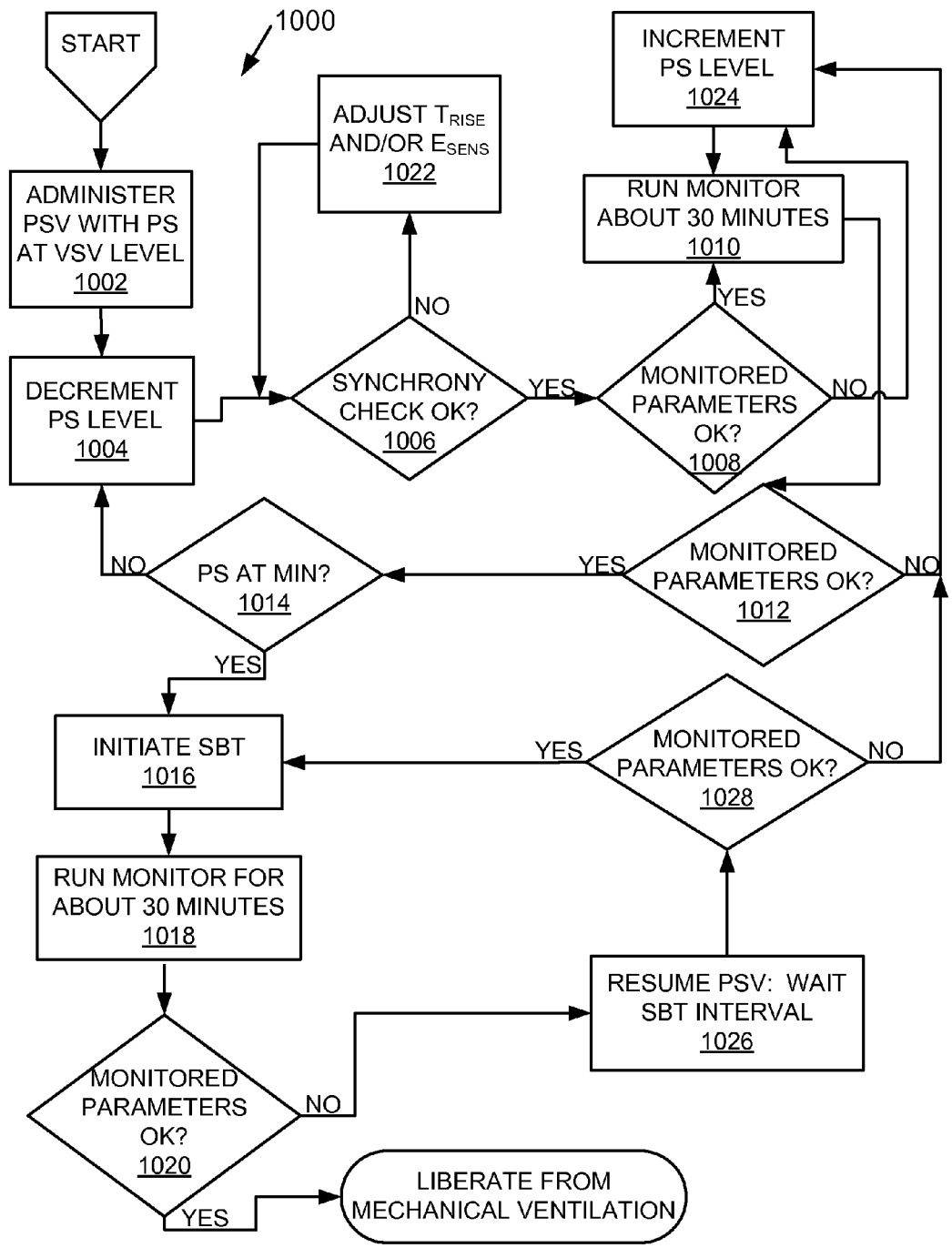
FIG. 10 illustrates a method for automatically weaning a subject from a mechanical ventilator in a pressure support mode.

FIG. 10 is a flow chart illustrating a method 1000 for automatically weaning a subject from a mechanical ventilator in pressure support mode.

According to an embodiment, Step 1002 administers Pressure Support Ventilation (PVS) with Pressure Support (PS) at the most recent Volume Support Ventilation (VSV) pressure level. Step 1004 reduces the Pressure Support in decrements. In one embodiment, the PS level is reducing by decrements of about 2 hPa. Step 1006 determines if the ventilation is substantially synchronized with the breathing efforts of the subject. If Step 1006 determines that ventilation is substantially synchronized with the breathing efforts of the subject, Step 1008 determines if the subject monitored parameters, such as VS, $E_TCO_2$, or $S_PO_2$, are within a predetermined acceptable range. If Step 1008 determines that monitored parameters of the subject are not within the predetermined acceptable range, Step 1024 increases the PS level. In one embodiment, the PS level is increased by increments of 2 hPa. If Step 1008 determines that the ventilation of the subject is within the predetermined acceptable range, Step 1010 monitors the subject for a predetermined period of time, such as about 30 minutes. In one embodiment, the period of time may range from about 30 minutes to about 2 hours. After step 1010, Step 1012 determines if the subject parameters are within the predetermined acceptable ranges. As previously discussed, in one embodiment, the adequacy of ventilation may be determined by monitoring the $E_TCO_2$ level. If Step 1012 determines that the subject parameters are within the predetermined acceptable ranges, Step 1014 determines if PS is at a minimum. If yes, Step 1016 initiates a spontaneous breathing trial (SBT). Step 1018 monitors the subject for about 30 minutes. After step 1018, Step 1020 determines if the monitored parameters are within the predetermined acceptable range. If Step 1020 determines that the monitored parameters are within the predetermined acceptable range, an alert may be produced to alert a clinician that the subject may be removed from mechanical ventilation. If step 1006 determines that ventilation is not substantially synchronized with the breathing efforts of the subject, Step 1022 adjusts at least one of $T_{RISE}$ and $E_{SENS}$ after which Step 1006 is repeated. If step 1012 determines that the monitored parameters are not within the predetermined acceptable ranges, Step 1024 increases PS in increments after which step 1010 is repeated. If Step 1014 determines that the PS is not at a minimum, Step 1004 is repeated. If Step 1020 determines that the monitored parameters are not within their predetermined acceptable ranges, Step 1026 resumes PSV terminating the SBT interval. After Step 1026, Step 1028 determines if the monitored parameters are within the predetermined acceptable ranges. If Step 1028 determines that the monitored parameters are within the predetermined acceptable ranges, Step 1016 is repeated. If Step 1028 determines that the monitored parameters are not within the predetermined acceptable ranges, Step 1024 is repeated.

Figure 11:
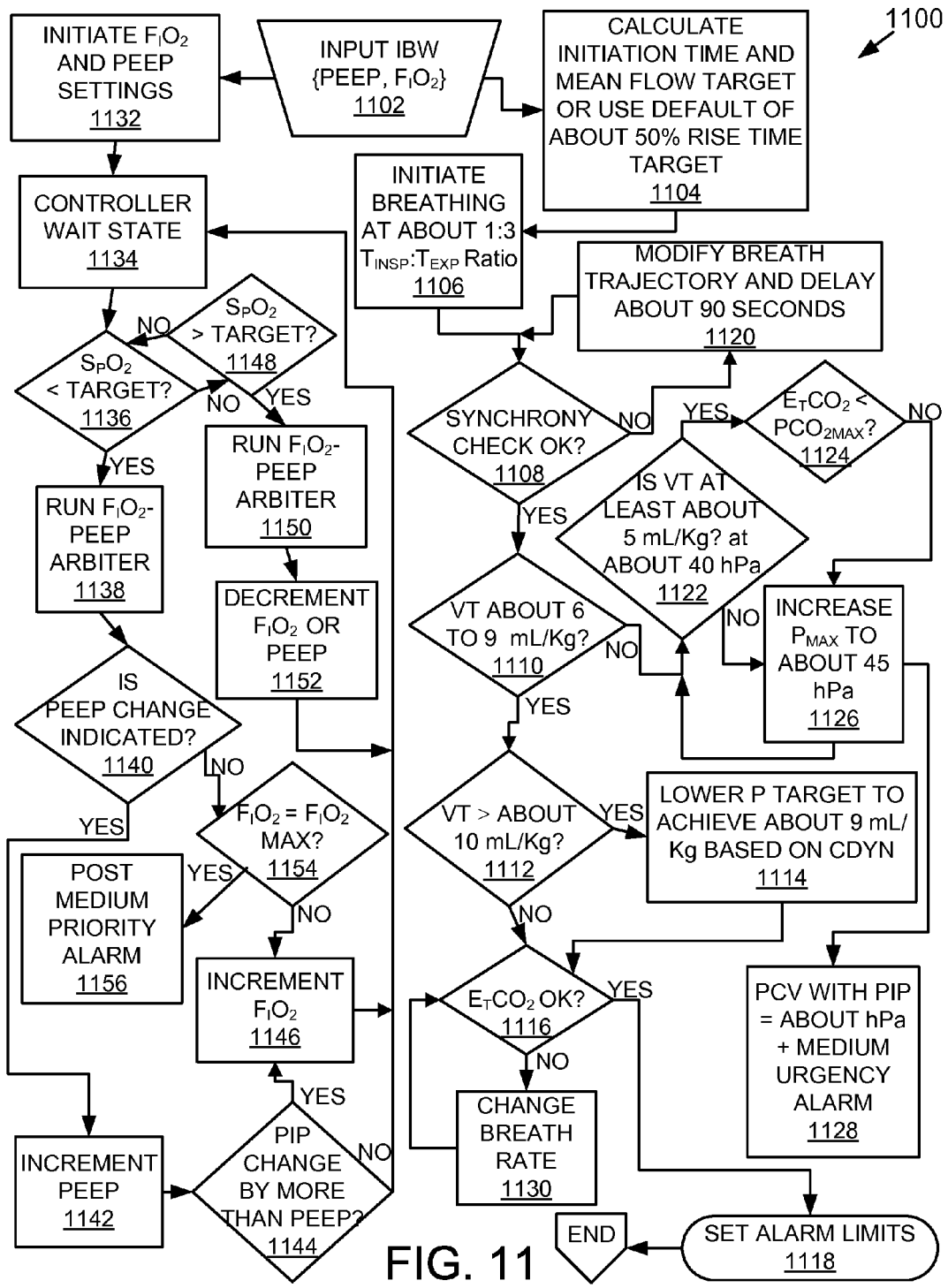
FIG. 11 illustrates a method for automatically initiating and adjusting mechanical ventilation.

FIG. 11 is a flow chart illustrating a method 1100 for automatically initiating and adjusting mechanical ventilation.

FIG. 11 is an amalgamation of the "Initiation" and "Management" phases. FIG. 11 essentially incorporates FIGS. 1, 2, 5 and 6. For further detail, please see the descriptions of these figures above.

Figure 12:
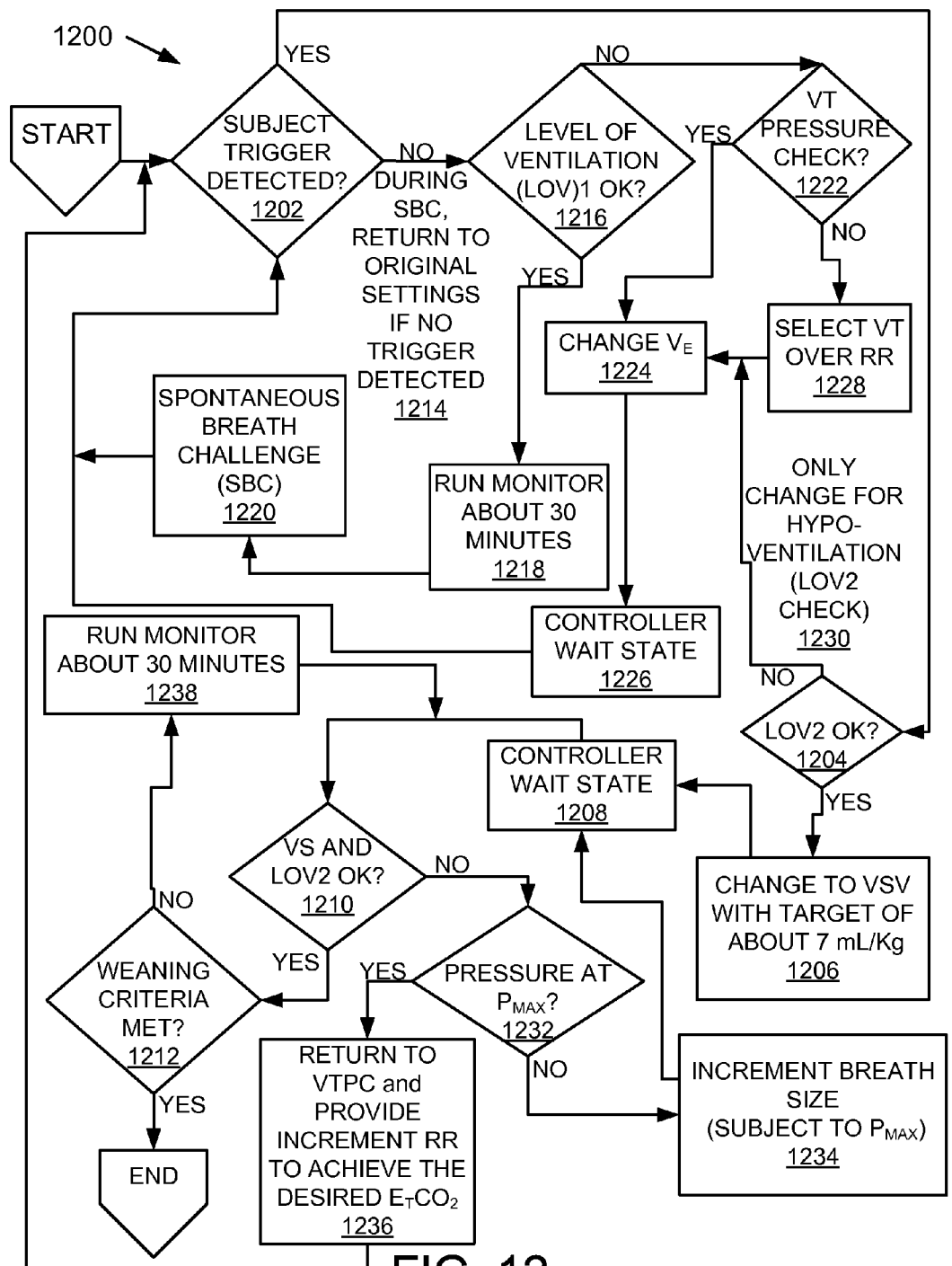
FIG. 12 illustrates a method for automatically controlling mechanical ventilation of a subject.

FIG. 12 is flow chart illustrating a method 1200 for automatically controlling ventilation of a subject.

FIG. 12 is an amalgamation of the "Transitioning To Subject Control" phase. FIG. 12 essentially incorporates FIGS. 7 and 8. For further detail, please see the descriptions of these figures above.

Figure 13:
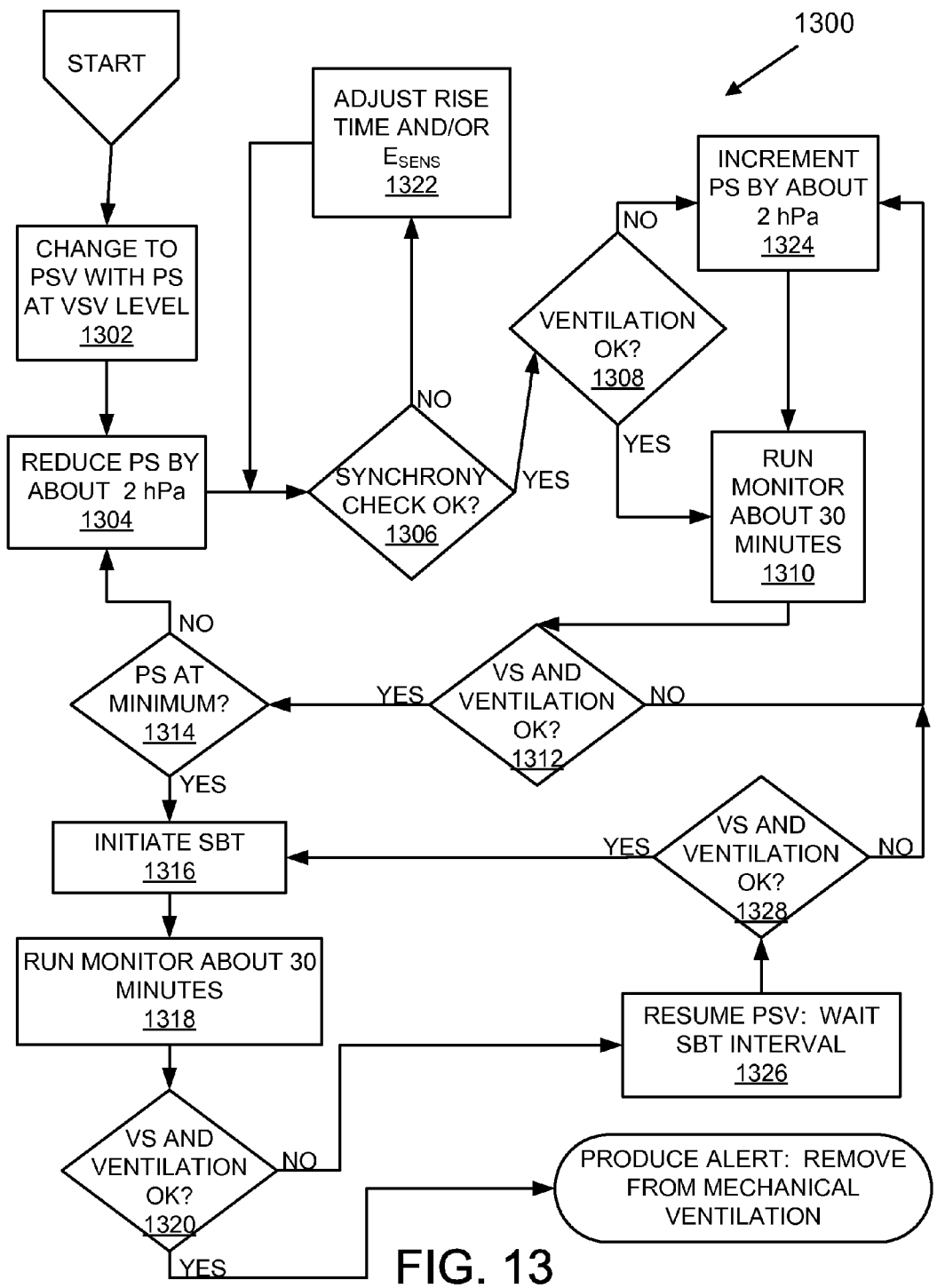
FIG. 13 illustrates a method for automatically weaning a subject from a mechanical ventilator in a volume support mode.

FIG. 13 is flow chart illustrating a method 1300 for automatically weaning a subject from a ventilator in a volume support mode.

FIG. 13 is an amalgamation of the "Weaning" phase. FIG. 13 essentially incorporates FIGS. 9 and 10. For further detail, please see the descriptions of these figures above.

It will be clear that the described device and method are well adapted to attain the ends and advantages mentioned as well as those inherent therein. Those skilled in the art will recognize that the method and device described within this specification may be implemented in many different manners and as such is not to be limited by the foregoing exemplified embodiments and examples. In other words, functional elements being performed by a single or multiple components, in various combinations of hardware and software, and individual functions can be distributed among software applications and even different hardware platforms. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the described technology. Numerous other changes may be made which will readily suggest themselves to those skilled in the art and which are encompassed in the spirit of the disclosure and as defined in the appended claims.

What is claimed is:

1. A method of automatically weaning a subject from a ventilator in volume support mode, comprising:
    measuring at least one of end tidal exhaled carbon dioxide concentration ($E_TCO_2$), volume size of breath delivered to the subject ($V_T$) and breath frequency;
    comparing at least one of measured $E_TCO_2$, $V_T$ and breath frequency with predetermined $E_TCO_2$, $V_T$ and breath frequency target ranges based on monitoring of subject parameters and an inputted ideal body weight (IBW) to determine if the subject is ready for weaning; and
    if one or more of the measured $E_TCO_2$, $V_T$ and breath frequency are within their respective target ranges for a predetermined period of time, determining that the subject is ready for weaning and then transitioning the ventilator from the volume support ventilation to pressure support ventilation to begin weaning.

2. The method of claim 1, wherein an initial pressure utilized in the pressure support ventilation is adjusted at a preset value below a target pressure utilized in said volume support ventilation.

3. The method of claim 2, further comprising reducing said initial pressure in a step wise manner over predetermined time intervals.

4. The method of claim 3, wherein said initial pressure is reduced by about 2 hPa over time intervals of about 15 minutes.

5. The method of claim 3, further comprising initiating a spontaneous breath trial.

6. The method of claim 5, wherein the subject maintains at least one physiological parameter at an acceptance criteria for a defined period of time during the spontaneous breath trial.

7. The method of claim 6, further comprising providing an alert that the subject can be withdrawn from mechanical ventilation.

8. The method of claim 5, further comprising adjusting ventilation parameters back to the volume support ventilation when the subject does not maintain at least one physiological parameter at an acceptable level for a defined period of time during the spontaneous breath trial.

* * * * *